(12) United States Patent
Strang et al.

(10) Patent No.: US 11,857,190 B2
(45) Date of Patent: Jan. 2, 2024

(54) SURGICAL STAPLER BUTTRESS WITH VARIABLE LENGTH FEATURE

(71) Applicant: Cilag GmbH International, Zug (CH)

(72) Inventors: Heather Strang, West Chester, OH (US); Jordan B. Wong, Cincinnati, OH (US); Michael J. Vendely, Lebanon, OH (US); Christopher J. Hess, Blue Ash, OH (US)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 17/462,451

(22) Filed: Aug. 31, 2021

(65) Prior Publication Data

US 2023/0064301 A1 Mar. 2, 2023

(51) Int. Cl.
*A61B 17/072* (2006.01)

(52) U.S. Cl.
CPC .......... *A61B 17/07292* (2013.01); *A61B 2017/0725* (2013.01); *A61B 2017/07285* (2013.01)

(58) Field of Classification Search
CPC ............ A61B 17/07292; A61B 17/072; A61B 17/07285
See application file for complete search history.

(56) References Cited

U.S. PATENT DOCUMENTS

| | | | |
|---|---|---|---|
| 7,380,696 B2 | 6/2008 | Shelton, IV et al. | |
| 7,665,646 B2 | 2/2010 | Prommersberger | |
| 8,210,411 B2 | 7/2012 | Yates et al. | |
| 8,408,439 B2 | 4/2013 | Huang et al. | |
| 8,453,914 B2 | 6/2013 | Laurent et al. | |
| 9,186,142 B2 | 11/2015 | Fanelli et al. | |
| 9,517,065 B2 | 12/2016 | Simms et al. | |
| 9,522,002 B2 * | 12/2016 | Chowaniec | A61B 17/072 |
| 9,622,746 B2 | 4/2017 | Simms et al. | |
| 9,717,497 B2 | 8/2017 | Zerkle et al. | |
| 9,795,379 B2 | 10/2017 | Leimbach et al. | |
| 9,808,248 B2 | 11/2017 | Hoffman | |
| 9,839,421 B2 | 12/2017 | Zerkle et al. | |
| 10,092,292 B2 | 10/2018 | Boudreaux et al. | |
| 10,166,023 B2 * | 1/2019 | Vendely | A61B 17/07207 |
| 10,349,939 B2 | 7/2019 | Shelton, IV et al. | |
| 10,349,940 B2 * | 7/2019 | Zeiner | A61B 17/068 |
| 11,033,269 B2 | 6/2021 | Vendely et al. | |
| 11,166,725 B2 | 11/2021 | Vendely et al. | |
| 11,432,817 B2 | 9/2022 | Barton et al. | |
| 2012/0080336 A1 | 4/2012 | Shelton, IV et al. | |
| 2012/0289979 A1 * | 11/2012 | Eskaros | A61B 17/07292 606/151 |

(Continued)

OTHER PUBLICATIONS

International Search Report and Written Opinion dated Jan. 23, 2023 for Application No. PCT/IB2022/058109, 21 pgs.

*Primary Examiner* — Gloria R Weeks
(74) *Attorney, Agent, or Firm* — Frost Brown Todd LLP

(57) ABSTRACT

An assembly includes an applicator, which includes a housing defining a gap configured to receive an end effector jaw of a surgical stapler. The applicator also includes a platform positioned within the gap. The assembly also includes a buttress assembly having a first length and positioned on the platform. The assembly further includes a trimming feature presented by the applicator or the buttress assembly, and configured to facilitate trimming of the buttress assembly from the first length to a predetermined second length.

20 Claims, 23 Drawing Sheets

(56) References Cited

U.S. PATENT DOCUMENTS

| | | | |
|---|---|---|---|
| 2017/0056017 A1* | 3/2017 | Vendely | A61B 50/30 |
| 2018/0235617 A1* | 8/2018 | Shelton, IV | A61B 50/20 |
| 2021/0106329 A1* | 4/2021 | Williams | A61B 17/11 |
| 2021/0290227 A1* | 9/2021 | Mandula | A61B 17/0686 |
| 2022/0079581 A1* | 3/2022 | Zeiner | A61B 17/072 |
| 2022/0167981 A1* | 6/2022 | Shelton, IV | A61B 17/07207 |

* cited by examiner

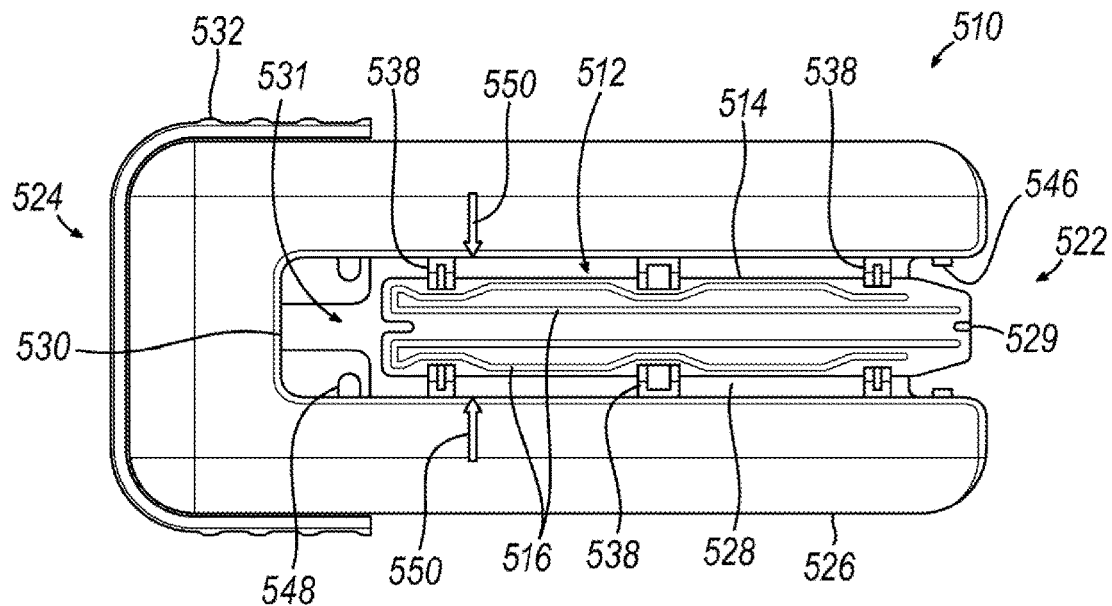
FIG. 16
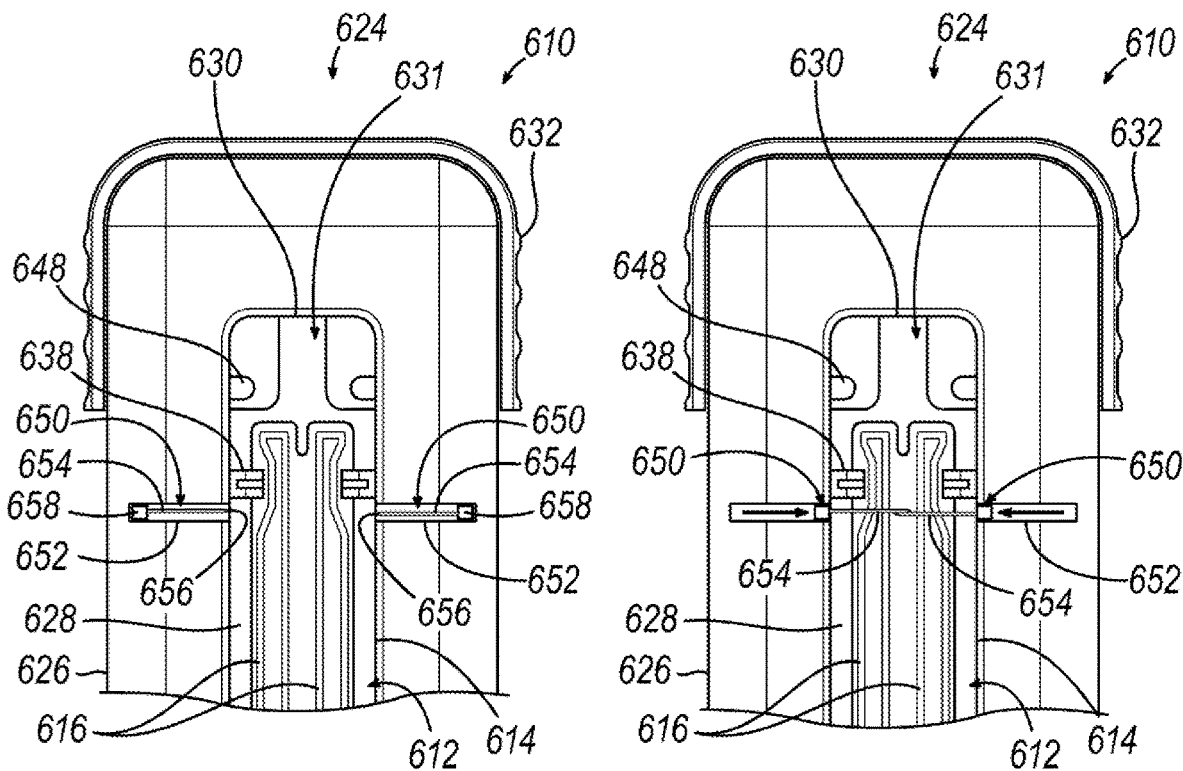
FIG. 17A  FIG. 17B

SURGICAL STAPLER BUTTRESS WITH VARIABLE LENGTH FEATURE

BACKGROUND

In some surgical settings, endoscopic surgical instruments may be preferred over traditional open surgical devices in order to make use of a smaller incision in the patient, which may reduce post-operative recovery time and complications. Some endoscopic surgical instruments may be suitable for placement of a distal end effector at a desired surgical site through the cannula of a trocar. These distal end effectors may engage tissue in a number of ways to achieve a diagnostic or therapeutic effect (e.g., endocutter, grasper, cutter, stapler, clip applier, access device, drug/gene therapy delivery device, and energy delivery device using ultrasound, RF, laser, etc.). Endoscopic surgical instruments may include a shaft between the end effector and a handle portion, which is manipulated by the clinician. Such a shaft may enable insertion to a desired depth and rotation about the longitudinal axis of the shaft, thereby facilitating positioning of the end effector within the patient. Positioning of an end effector may be further facilitated through inclusion of one or more articulation joints or features, enabling the end effector to be selectively articulated or otherwise deflected relative to the longitudinal axis of the shaft.

Examples of endoscopic surgical instruments include surgical staplers. Some such staplers are operable to clamp down on layers of tissue, cut through the clamped layers of tissue, and drive staples through the layers of tissue to substantially seal the severed layers of tissue together near the severed ends of the tissue layers. Merely exemplary surgical staplers are disclosed in U.S. Pat. No. 7,380,696, entitled "Articulating Surgical Stapling Instrument Incorporating a Two-Piece E-Beam Firing Mechanism," issued Jun. 3, 2008; U.S. Pat. No. 8,408,439, entitled "Surgical Stapling Instrument with An Articulatable End Effector," issued Apr. 2, 2013; and U.S. Pat. No. 8,453,914, entitled "Motor-Driven Surgical Cutting Instrument with Electric Actuator Directional Control Assembly," issued Jun. 4, 2013. The disclosure of each of the above-cited U.S. patents and U.S. patent Publications is incorporated by reference herein.

Surgical staplers may also be used in open procedures and/or other non-endoscopic procedures. By way of example only, a surgical stapler may be inserted through a thoracotomy and thereby between a patient's ribs to reach one or more organs in a thoracic surgical procedure that does not use a trocar as a conduit for the stapler. For instance, the vessels leading to an organ may be severed and closed by a stapler before removal of the organ from the thoracic cavity. Of course, surgical staplers may be used in various other settings and procedures.

While various kinds of surgical stapling instruments and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 16 depicts a top plan view of another exemplary buttress applicator for carrying and applying a buttress assembly, and having a laterally-opposed pair of visual indicia for facilitating trimming of the buttress assembly to a predetermined length;

FIG. 17A depicts a top plan view of another exemplary buttress applicator for carrying and applying a buttress assembly, and having a laterally-opposed pair of cutting elements slidable within respective grooves for facilitating trimming of the buttress assembly to a predetermined length, showing the cutting elements in a retracted state;

FIG. 17B depicts a top plan view of the buttress applicator of FIG. 17A, showing the cutting elements in an extended state;

Figure 1:
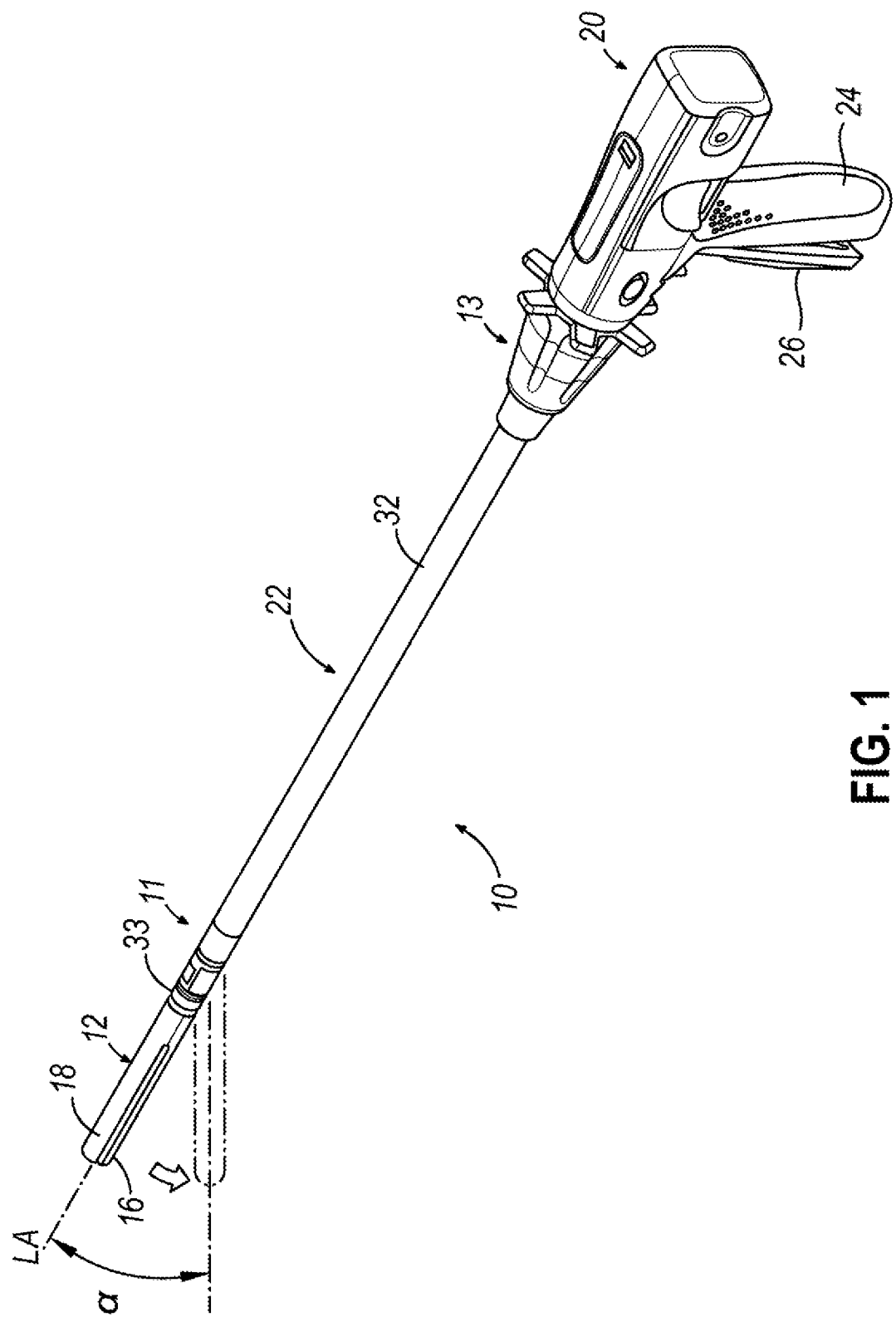
FIG. 1 depicts a perspective view of an exemplary surgical stapling instrument.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a human or robotic operator of the surgical instrument. The term "proximal"

refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument. In addition, the terms "upper," "lower," "lateral," "transverse," "bottom," "top," are relative terms to provide additional clarity to the figure descriptions provided below. The terms "upper," "lower," "lateral," "transverse," "bottom," "top," are thus not intended to unnecessarily limit the invention described herein.

I. Exemplary Surgical Stapler

FIGS. 1-7 depict an exemplary surgical stapling and severing instrument (10) that is sized for insertion through a trocar cannula or an incision (e.g., thoracotomy, etc.) to a surgical site in a patient for performing a surgical procedure. Instrument (10) of the present example includes a handle portion (20) connected to a shaft (22), which distally terminates in an articulation joint (11), which is further coupled with an end effector (12). Once articulation joint (11) and end effector (12) are inserted through the cannula passageway of a trocar, articulation joint (11) may be remotely articulated, as depicted in phantom in FIG. 1, by an articulation control (13), such that end effector (12) may be deflected from the longitudinal axis (LA) of shaft (22) at a desired angle (a). End effector (12) of the present example includes a lower jaw (16) that includes a staple cartridge (37), and an upper jaw in the form of a pivotable anvil (18).

Handle portion (20) includes a pistol grip (24) and a closure trigger (26). Closure trigger (26) is pivotable toward pistol grip (24) to cause clamping, or closing, of the anvil (18) toward lower jaw (16) of end effector (12). Such closing of anvil (18) is provided through a closure tube (32) and a closure ring (33), which both longitudinally translate relative to handle portion (20) in response to pivoting of closure trigger (26) relative to pistol grip (24). Closure tube (32) extends along the length of shaft (22); and closure ring (33) is positioned distal to articulation joint (11). Articulation joint (11) is operable to communicate/transmit longitudinal movement from closure tube (32) to closure ring (33).

Figure 2:
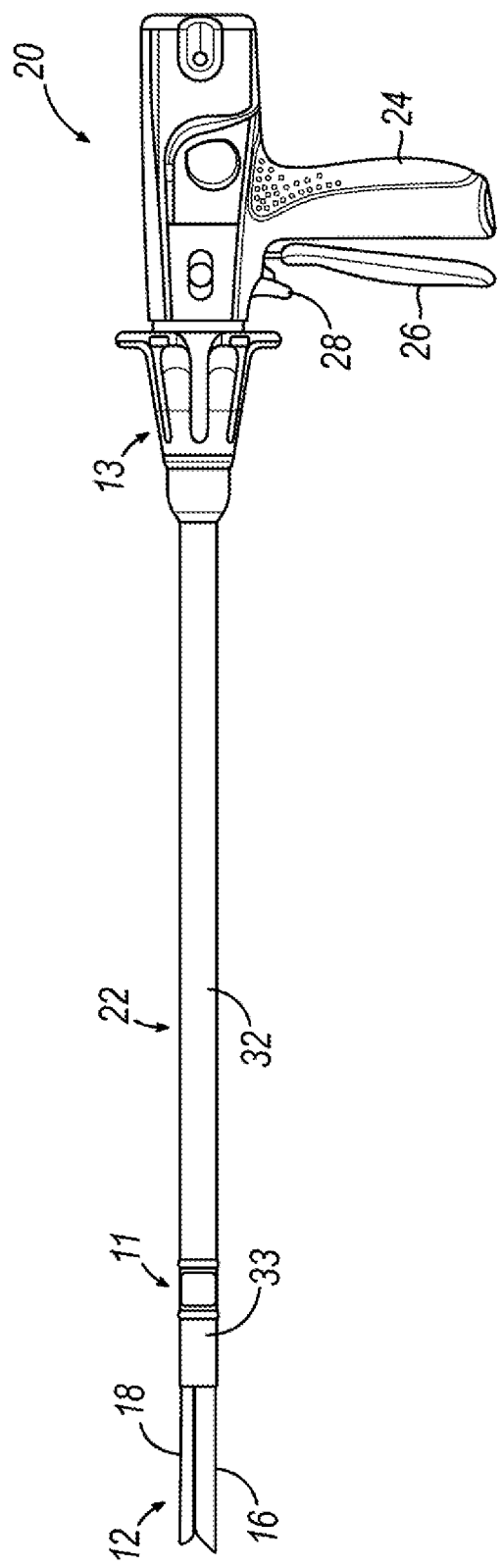
FIG. 2 depicts a side elevational view of the instrument of FIG. 1.

As shown in FIG. 2, handle portion (20) also includes a firing trigger (28). An elongate member (not shown) longitudinally extends through shaft (22) and communicates a longitudinal firing motion from handle portion (20) to a firing beam (14) in response to actuation of firing trigger (28). This distal translation of firing beam (14) causes the stapling and severing of clamped tissue in end effector (12), as will be described in greater detail below.

As shown in FIGS. 3-6, end effector (12) employs a firing beam (14) that includes a transversely oriented upper pin (38), a firing beam cap (44), a transversely oriented middle pin (46), and a distally presented cutting edge (48). Upper pin (38) is positioned and translatable within a longitudinal anvil slot (42) of anvil (18). Firing beam cap (44) slidably engages a lower surface of lower jaw (16) by having firing beam (14) extend through lower jaw slot (45) (shown in FIG. 4B) that is formed through lower jaw (16). Middle pin (46) slidingly engages a top surface of lower jaw (16), cooperating with firing beam cap (44).

Figure 3:
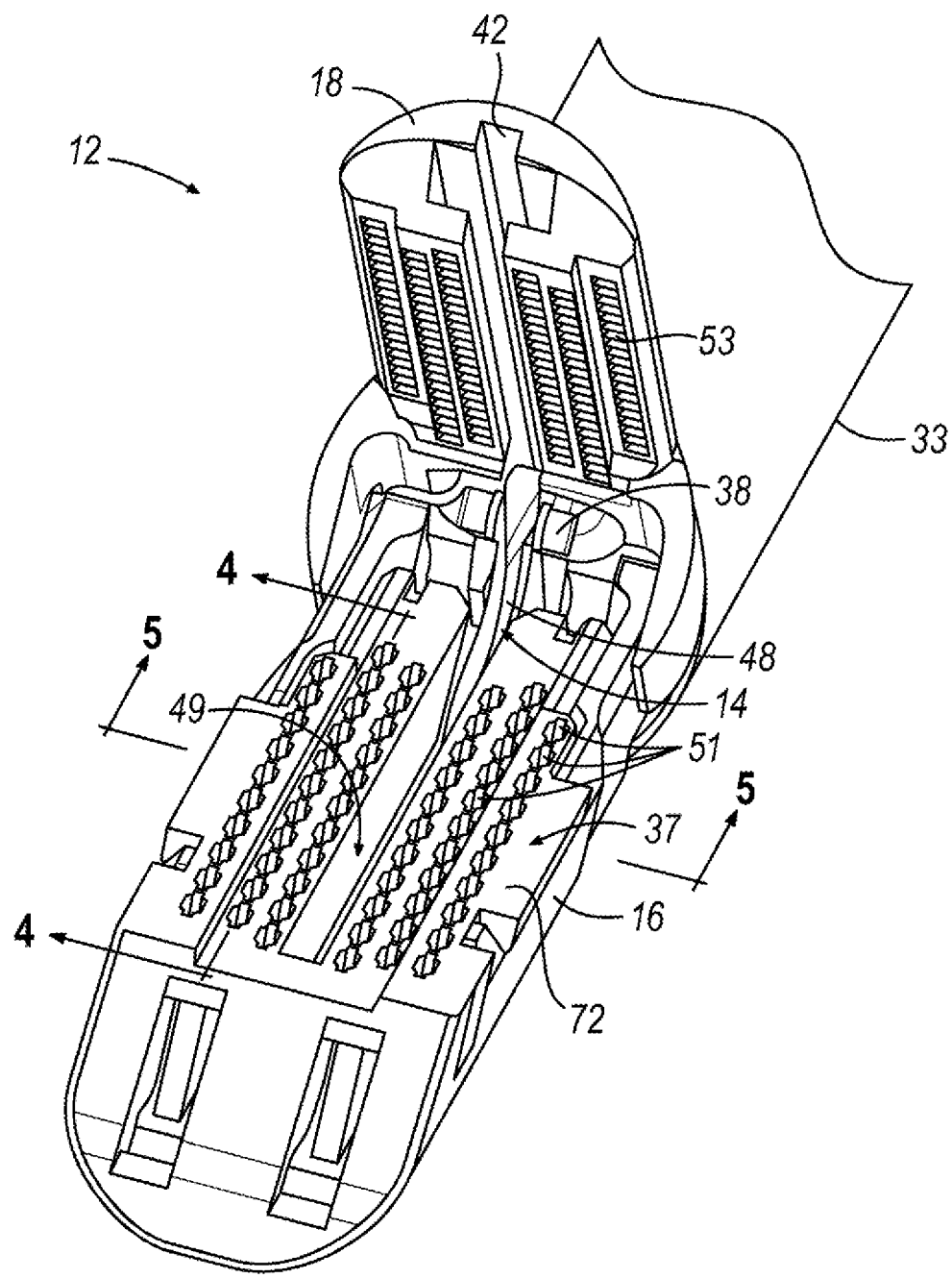
FIG. 3 depicts a perspective view of an end effector of the instrument of FIG. 1 in an open state.
Figure 4A:
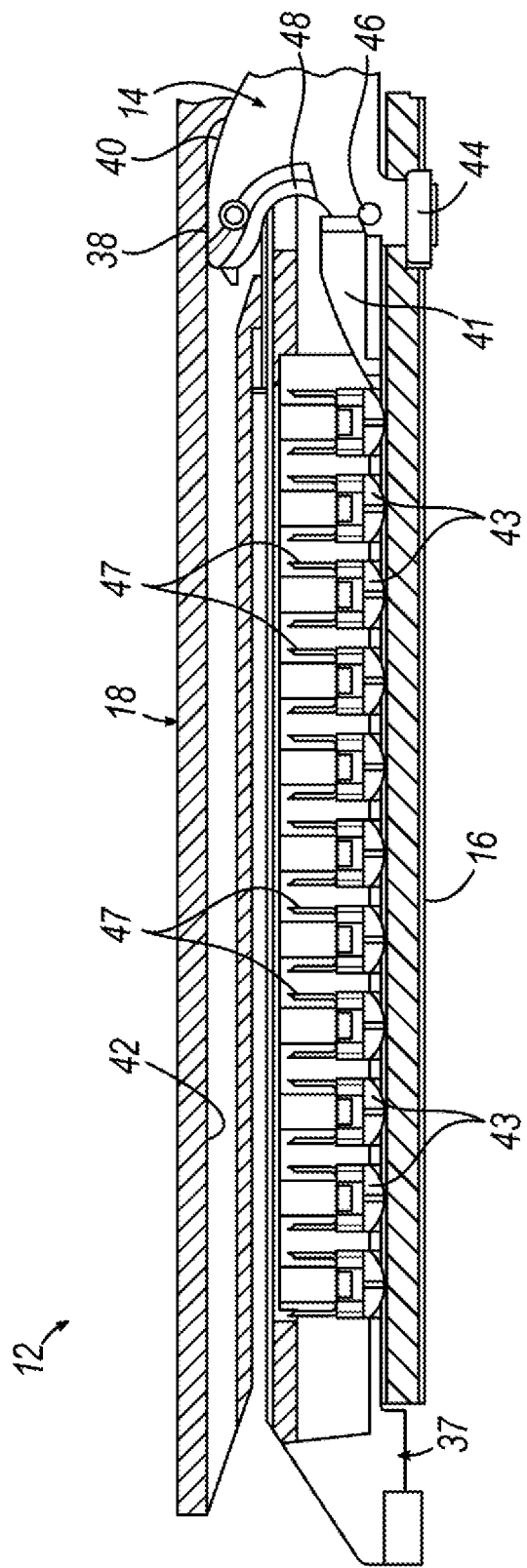
FIG. 4A depicts a side cross-sectional view of the end effector of FIG. 3, taken along line 4-4 of FIG. 3, with a firing beam in a proximal position.
Figure 4B:
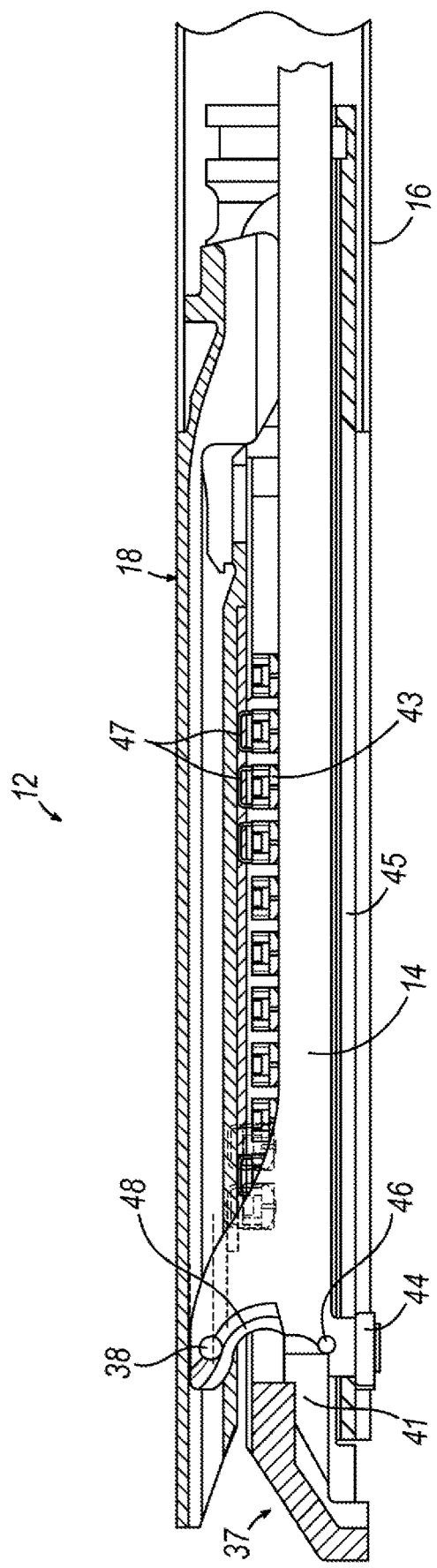
FIG. 4B depicts a side cross-sectional view of the end effector of FIG. 3, taken along line 4-4 of FIG. 3, with the firing beam in a distal position.
Figure 5:
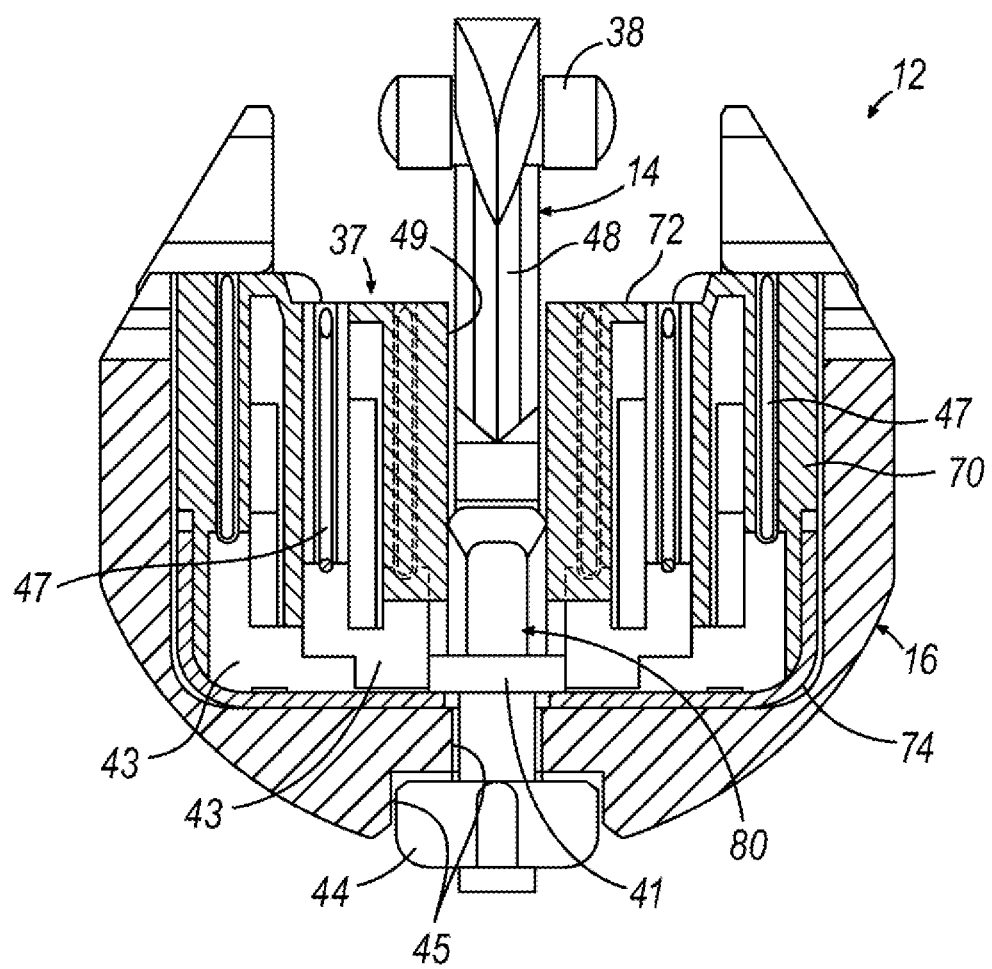
FIG. 5 depicts an end cross-sectional view of the end effector of FIG. 3, taken along line 5-5 of FIG. 3.
Figure 6:
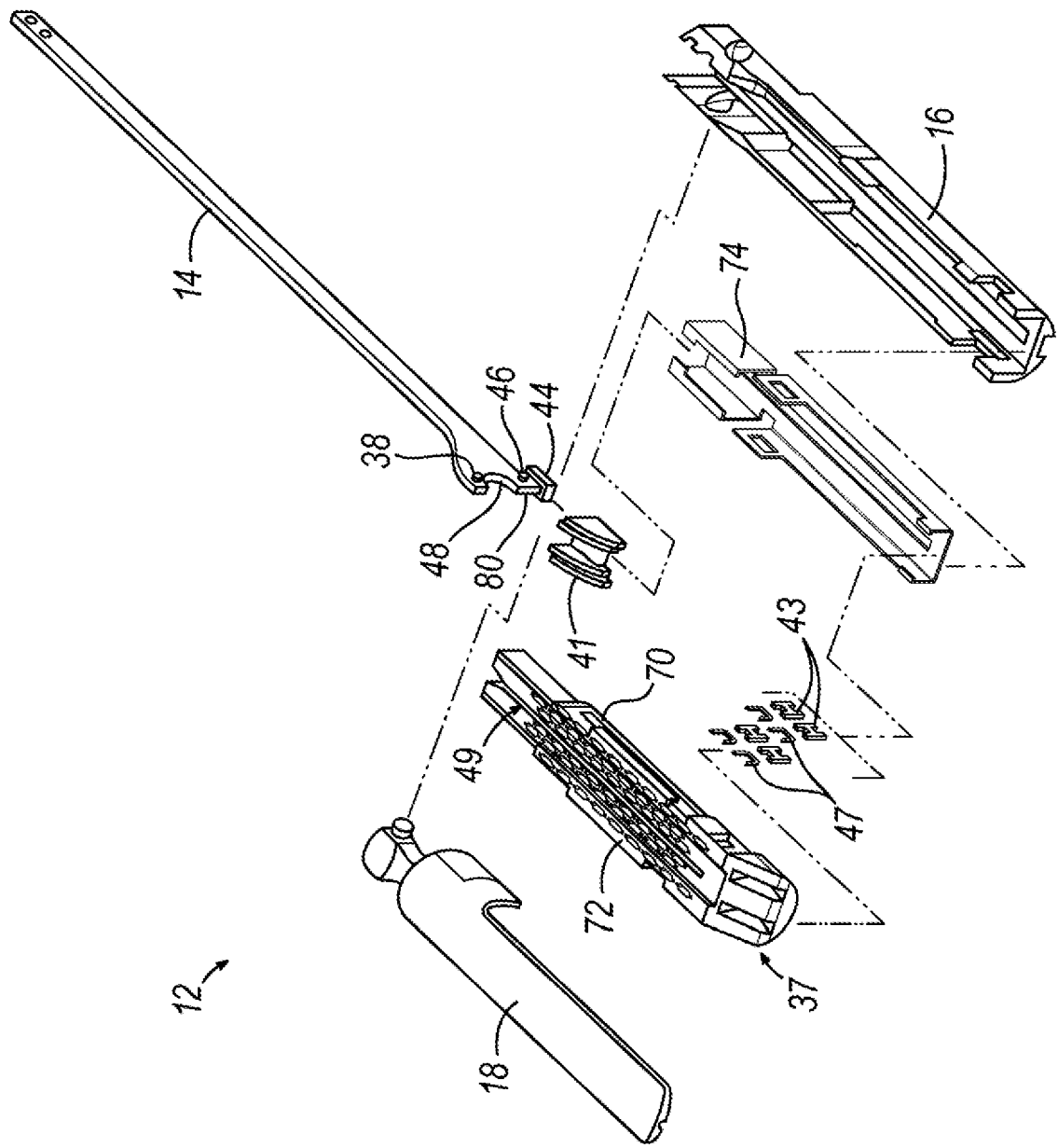
FIG. 6 depicts an exploded perspective view of the end effector of FIG. 3.

FIG. 3 shows firing beam (14) of the present example proximally positioned and anvil (18) pivoted to an open configuration, allowing an unspent staple cartridge (37) to be removably installed into a channel of lower jaw (16). As best seen in FIGS. 5-6, staple cartridge (37) of the present example includes a cartridge body (70), which presents an upper deck (72) and is coupled with a lower cartridge tray (74). As best seen in FIG. 3, a vertical slot (49) extends longitudinally through a portion of staple cartridge body (70). As also best seen in FIG. 3, three rows of staple apertures (51) are formed through upper deck (72) on each lateral side of vertical slot (49). As shown in FIGS. 4A-6, a wedge sled (41) and a plurality of staple drivers (43) are captured between cartridge body (70) and tray (74), with wedge sled (41) being located proximal to staple drivers (43). Wedge sled (41) is movable longitudinally within staple cartridge (37); while staple drivers (43) are movable vertically within staple cartridge (37). Staples (47) are also positioned within cartridge body (70), above corresponding staple drivers (43). Each staple (47) is driven vertically within cartridge body (70) by a staple driver (43) to drive staple (47) out through an associated staple aperture (51). As best seen in FIGS. 4A-4B and 6, wedge sled (41) presents inclined cam surfaces that urge staple drivers (43) upwardly as wedge sled (41) is driven distally through staple cartridge (37).

With end effector (12) closed, as depicted in FIGS. 4A-4B by distally advancing closure tube (32) and closure ring (33), firing beam (14) is then advanced distally into engagement with anvil (18) by having upper pin (38) enter longitudinal anvil slot (42). A pusher block (80) (shown in FIG. 5) located at the distal end of firing beam (14) pushes wedge sled (41) distally as firing beam (14) is advanced distally through staple cartridge (37) when firing trigger (28) is actuated. During such firing, cutting edge (48) of firing beam (14) enters vertical slot (49) of staple cartridge (37), severing tissue clamped between staple cartridge (37) and anvil (18). As shown in FIGS. 4A-4B, middle pin (46) and pusher block (80) together actuate staple cartridge (37) by entering into vertical slot (49) within staple cartridge (37), driving wedge sled (41) into upward camming contact with staple drivers (43), which in turn drives staples (47) out through staple apertures (51) and into forming contact with staple forming pockets (53) (shown in FIG. 3) on the inner surface of anvil (18). FIG. 4B depicts firing beam (14) fully distally translated after completing severing and stapling of tissue. Staple forming pockets (53) are intentionally omitted from the view in FIGS. 4A-4B but are shown in FIG. 3. Anvil (18) is intentionally omitted from the view in FIG. 5.

Figure 7:
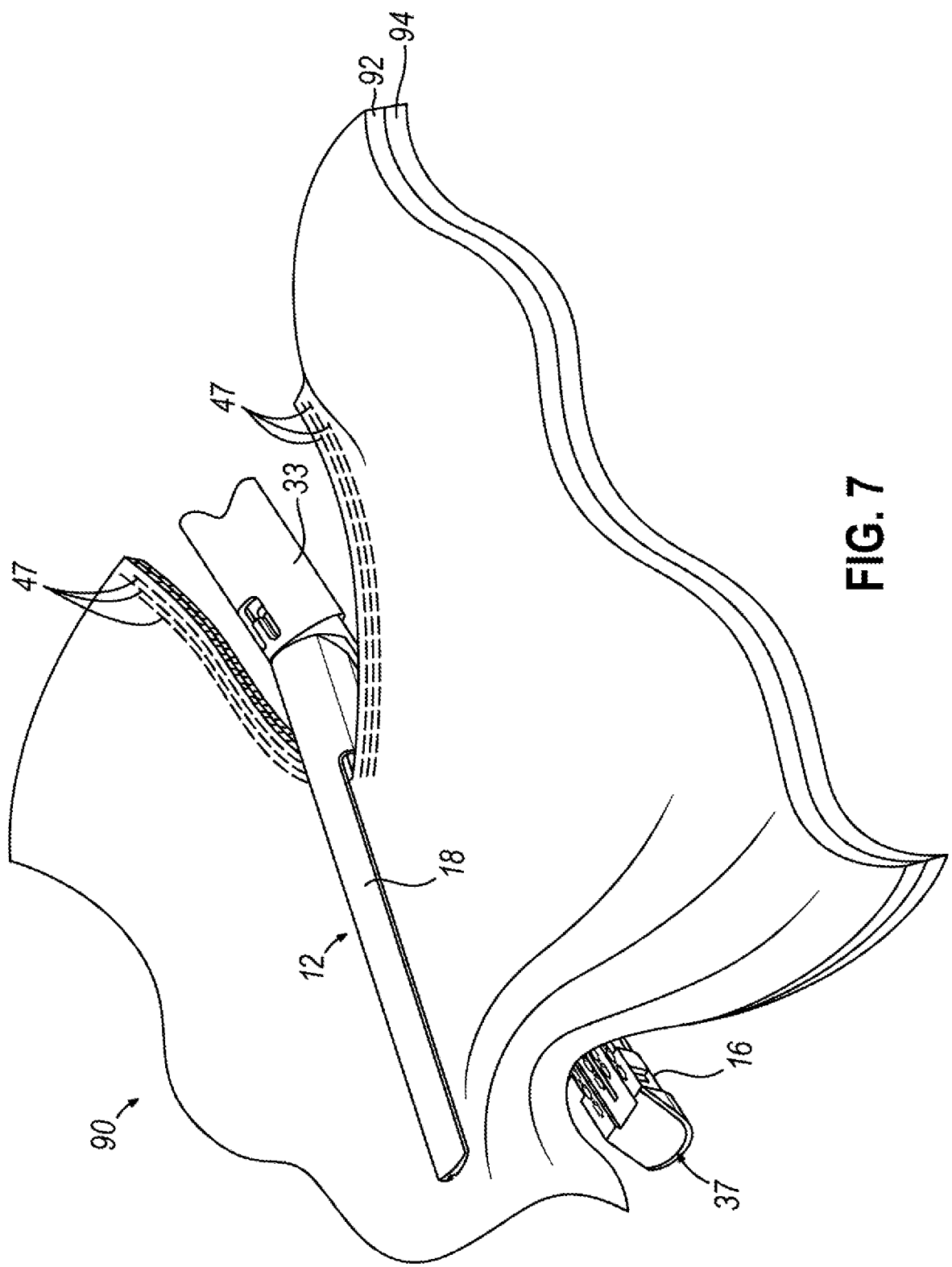
FIG. 7 depicts a perspective view of the end effector of FIG. 3, positioned at tissue and having been actuated once in the tissue.

FIG. 7 shows end effector (12) having been actuated through a single firing stroke through tissue (90). Cutting edge (48) (obscured in FIG. 7) has cut through tissue (90), while staple drivers (43) have driven three alternating rows of staples (47) through the tissue (90) on each side of the cut line produced by cutting edge (48). After the first firing stroke is complete, end effector (12) is withdrawn from the patient, spent staple cartridge (37) is replaced with a new staple cartridge (37), and end effector (12) is then again inserted into the patient to reach the stapling site for further cutting and stapling. This process may be repeated until the desired quantity and pattern of firing strokes across the tissue (90) has been completed.

Instrument (10) may be further constructed and operable in accordance with any of the teachings of the following references, the disclosures of which are incorporated by reference herein: U.S. Pat. No. 8,210,411, entitled "Motor-Driven Surgical Instrument," issued Jul. 3, 2012; U.S. Pat. No. 9,186,142, entitled "Surgical Instrument End Effector Articulation Drive with Pinion and Opposing Racks," issued on Nov. 17, 2015; U.S. Pat. No. 9,517,065, entitled "Integrated Tissue Positioning and Jaw Alignment Features for Surgical Stapler," issued Dec. 13, 2016; U.S. Pat. No.

9,622,746, entitled "Distal Tip Features for End Effector of Surgical Instrument," issued Apr. 18, 2017; U.S. Pat. No. 9,717,497, entitled "Lockout Feature for Movable Cutting Member of Surgical Instrument," issued Aug. 1, 2017; U.S. Pat. No. 9,795,379, entitled "Surgical Instrument with Multi-Diameter Shaft," issued Oct. 24, 2017; U.S. Pat. No. 9,808,248, entitled "Installation Features for Surgical Instrument End Effector Cartridge," issued Nov. 7, 2017; U.S. Pat. No. 9,839,421, entitled "Jaw Closure Feature for End Effector of Surgical Instrument," issued Dec. 12, 2017; and/or U.S. Pat. No. 10,092,292, entitled "Staple Forming Features for Surgical Stapling Instrument," issued Oct. 9, 2018.

II. Exemplary Buttress Assembly and Buttress Applier Cartridge

In some instances, it may be desirable to equip end effector (12) of surgical instrument (10) with an adjunct material, such as a buttress, to reinforce the mechanical fastening of tissue provided by staples (47). Such a buttress may prevent the applied staples (47) from pulling through the tissue and may otherwise reduce a risk of tissue tearing at or near the site of applied staples (47). In addition to or as an alternative to providing structural support and integrity to a line of staples (47), a buttress may provide various other kinds of effects such as spacing or gap-filling, administration of therapeutic agents, and/or other effects. In some instances, a buttress may be provided on upper deck (72) of staple cartridge (37). As described above, deck (72) houses staples (47), which are driven by staple driver (43). In some other instances, a buttress may be provided on the surface of anvil (18) that faces staple cartridge (37). It should also be understood that a first buttress may be provided on upper deck (72) of staple cartridge (37) while a second buttress is provided on anvil (18) of the same end effector (12).

Various examples of forms that a buttress may take will be described in greater detail below. Various ways in which a buttress may be secured to a staple cartridge (37) or an anvil (18) will also be described in greater detail below. Exemplary buttress assemblies, exemplary materials and techniques for applying buttress assemblies, and exemplary buttress applier cartridges may be configured in accordance with at least some of the teachings of U.S. Pat. No. 10,166,023, entitled "Method of Applying a Buttress to a Surgical Stapler End Effector," issued Jan. 1, 2019; and/or in U.S. Pat. No. 10,349,939, entitled "Method of Applying a Buttress to a Surgical Stapler," issued Jul. 16, 2019, the disclosures of which are incorporated by reference herein.

A. Exemplary Composition of Buttress Assembly

Figure 8:
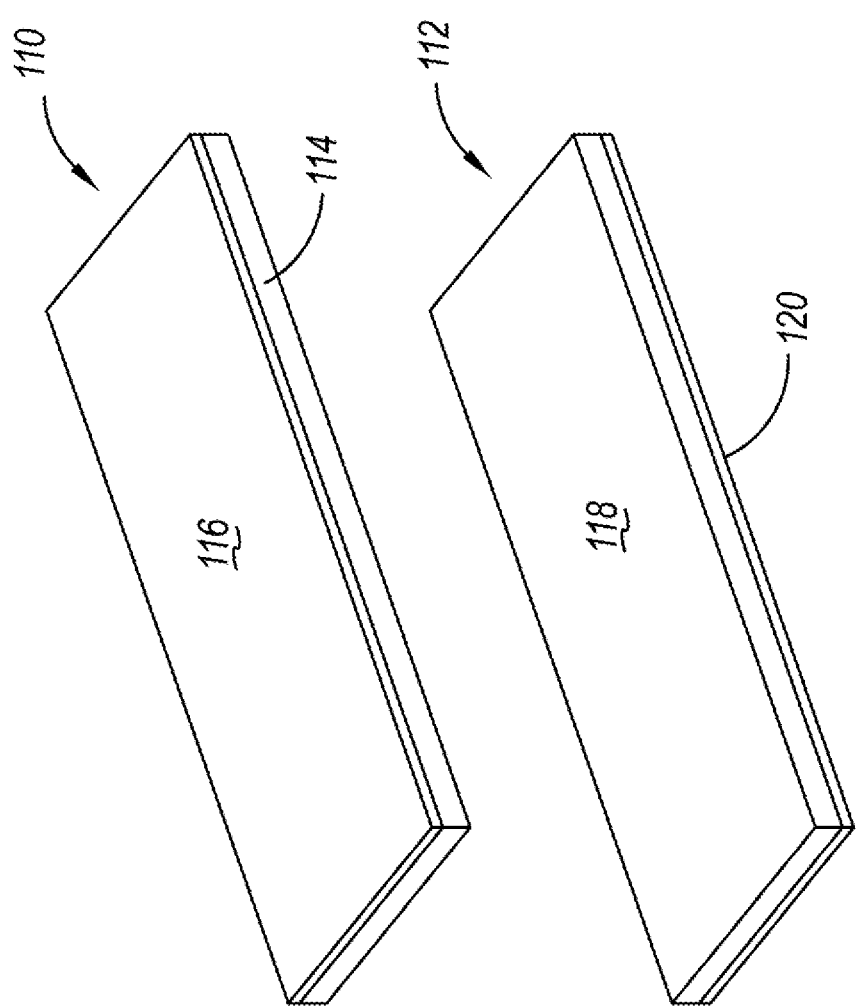
FIG. 8 depicts a perspective view of an exemplary pair of buttress assemblies, each of which may be applied to a jaw of the end effector of FIG. 3.

FIG. 8 shows an exemplary pair of buttress assemblies (110, 112) (each also referred to individually as a "buttress"). Buttress assembly (110) of this example comprises a buttress body (114) and an upper adhesive layer (116). Similarly, buttress assembly (112) comprises a buttress body (118) and a lower adhesive layer (120). In the present example, each buttress body (114, 118) comprises a strong yet flexible material configured to structurally support a line of staples (47). By way of example only, each buttress body (114, 118) may comprise a mesh of polyglactin 910 material by Ethicon, Inc. of Somerville, N.J. Alternatively, any other suitable materials or combinations of materials may be used in addition to or as an alternative to polyglactin 910 material to form each buttress body (114, 118).

Each buttress body (114, 118) may comprise a material including, for example, a hemostatic agent such as fibrin to assist in coagulating blood and reduce bleeding at the severed and/or stapled surgical site along tissue ($T_1$, $T_2$). As another merely illustrative example, each buttress body (114, 118) may comprise other adjuncts or hemostatic agents such as thrombin may be used such that each buttress body (114, 118) may assist to coagulate blood and reduce the amount of bleeding at the surgical site. Other adjuncts or reagents that may be incorporated into each buttress body (114, 118) may further include but are not limited to medical fluid or matrix components.

In the present example, adhesive layer (116) is provided on buttress body (114) to adhere buttress body (114) to underside (124) of anvil (18). Similarly, adhesive layer (120) is provided on buttress body (118) to adhere buttress body (118) to upper deck (72) of staple cartridge (37). Such an adhesive material may provide proper positioning of buttress body (114, 118) before and during actuation of end effector (12); then allow buttress body (114, 118) to separate from end effector (12) after end effector (12) has been actuated, without causing damage to buttress body (114, 118) that is substantial enough to compromise the proper subsequent functioning of buttress body (114, 118).

B. Exemplary Stapling of Tissue with Buttress Assemblies

Figure 9:
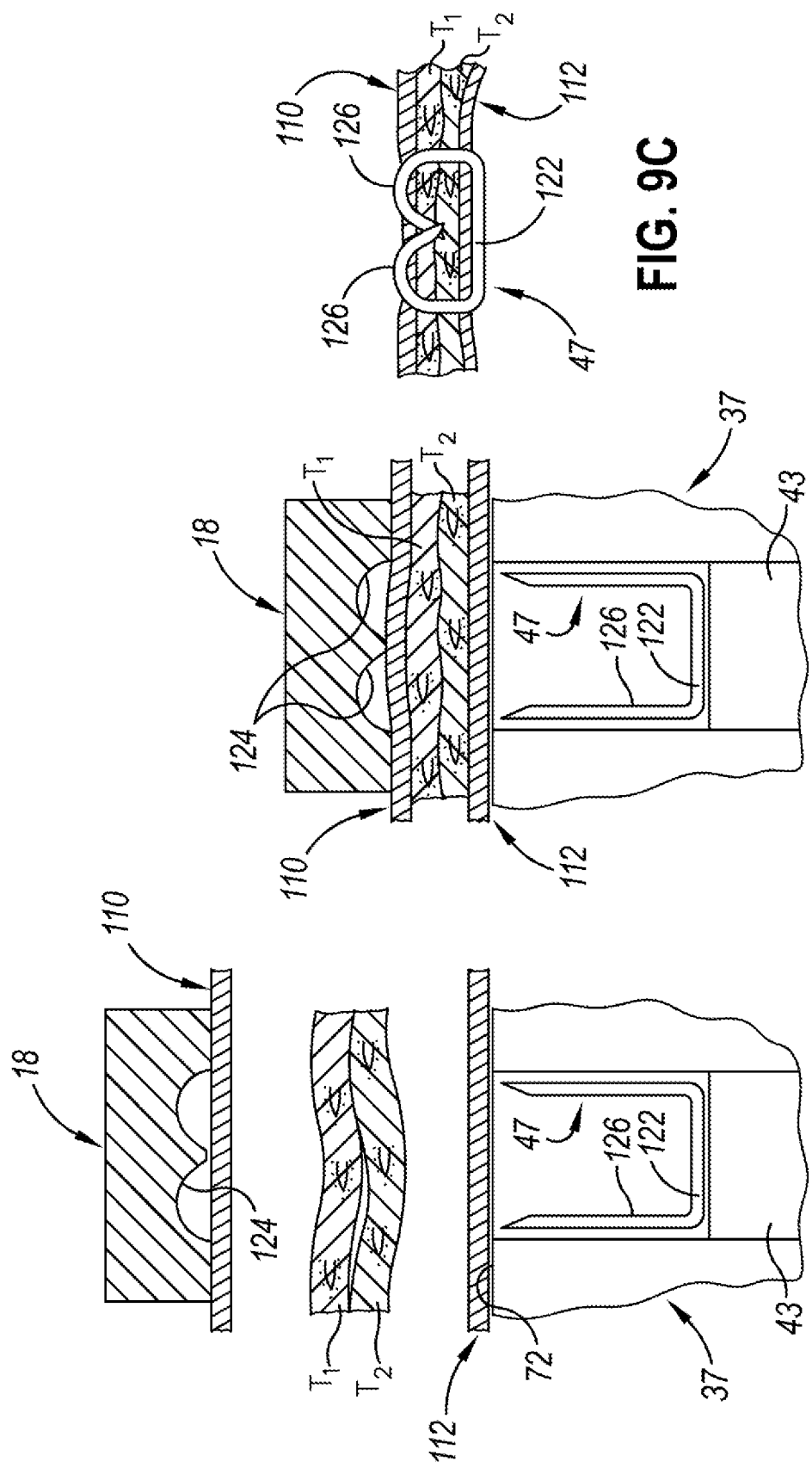
FIG. 9A depicts a cross-sectional end view of a portion of the end effector of FIG. 3 with the buttress assemblies of FIG. 8 applied to the upper and lower jaws of the end effector, showing the end effector jaws in an open state with tissue positioned between the upper and lower jaws.
FIG. 9B depicts a cross-sectional end view of the end effector and buttress assemblies of FIG. 9A, showing the end effector jaws in a closed state on the tissue.
FIG. 9C depicts a cross-sectional view of a formed staple and the buttress assemblies of FIG. 9A after having been secured to the tissue by the end effector of FIG. 3.

FIGS. 9A-9C show an exemplary sequence in which surgical stapler end effector (12), which has been loaded with buttress assemblies (110, 112), is actuated to drive staples (47) through two opposed layers of tissue ($T_1$, $T_2$), with buttress assemblies (110, 112) being secured to the same layers of tissue ($T_1$, $T_2$) by staples (47). In particular, FIG. 9A shows layers of tissue ($T_1$, $T_2$) positioned between anvil (18) and staple cartridge (37), with anvil (18) in the open position. Buttress assembly (110) is adhered to underside (124) of anvil (18) via adhesive layer (116); while buttress assembly (112) is adhered to upper deck (72) of staple cartridge (37) via adhesive layer (120). Layers of tissue ($T_1$, $T_2$) are thus interposed between buttress assemblies (110, 112). Next, closure trigger (26) is pivoted toward pistol grip (24) to drive closure tube (32) and closure ring (33) distally. This drives anvil (18) to the closed position as shown in FIG. 9B. At this stage, layers of tissue ($T_1$, $T_2$) are compressed between anvil (18) and staple cartridge (37), with buttress assemblies (110, 112) engaging opposite surfaces of tissue layers ($T_1$, $T_2$). End effector (12) is then actuated as described above, driving staple (47) through buttress assemblies (110, 112) and tissue ($T_1$, $T_2$). As shown in FIG. 13C, crown (122) of driven staple (47) captures and retains buttress assembly (112) against layer of tissue ($T_2$). Deformed legs (126) of staple (47) capture and retain buttress assembly (110) against layer of tissue ($T_1$).

Figure 10:
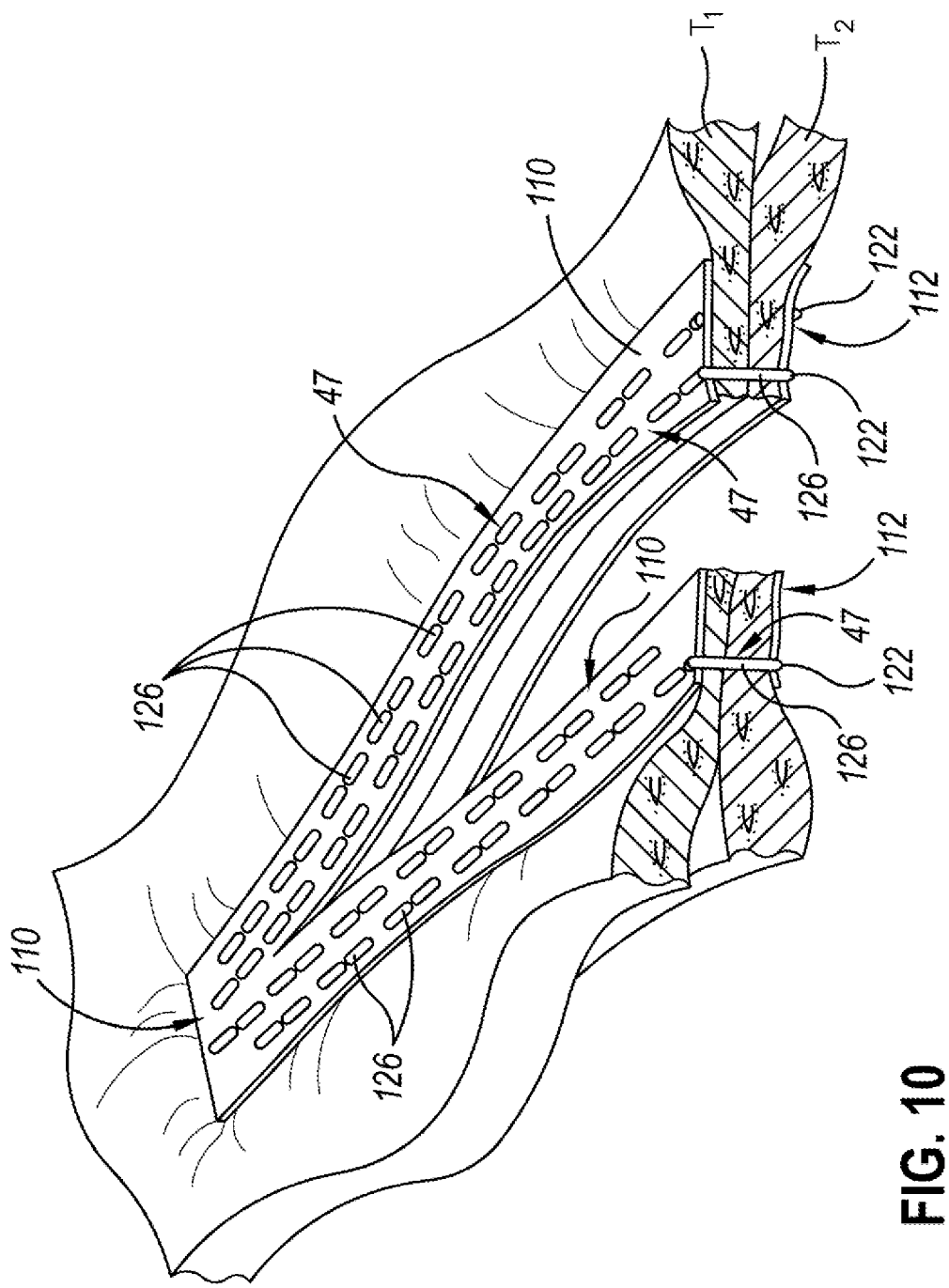
FIG. 10 depicts a perspective view of formed staples and the buttress assemblies of FIG. 9A after having been secured to the tissue by the end effector of FIG. 3.

A series of staples (47) similarly capture and retain buttress assemblies (110, 112) against layers of tissue ($T_1$, $T_2$), thereby securing buttress assemblies (110, 112) to tissue ($T_1$, $T_2$) as shown in FIG. 10. As end effector (12) is pulled away from tissue ($T_1$, $T_2$) after deploying staples (47) and buttress assemblies (110, 112), buttress assemblies (110, 112) disengage end effector such that buttress assemblies (110, 112) remain secured to tissue ($T_1$, $T_2$) with staples (47). Buttresses (110, 112) thus provides structural reinforcement to the lines of staples (47) formed in tissue ($T_1$, $T_2$). As can also be seen in FIG. 10, distally presented cutting edge (48) of firing beam (14) also cuts through a centerline of buttress tissue assemblies (110, 112), separating each buttress assembly (110, 112) into a corresponding pair of sections, such that each section remains secured to a respective severed region of tissue ($T_1$, $T_2$).

C. Exemplary Buttress Applier Cartridge with Active Retainer Arms

Figure 11:
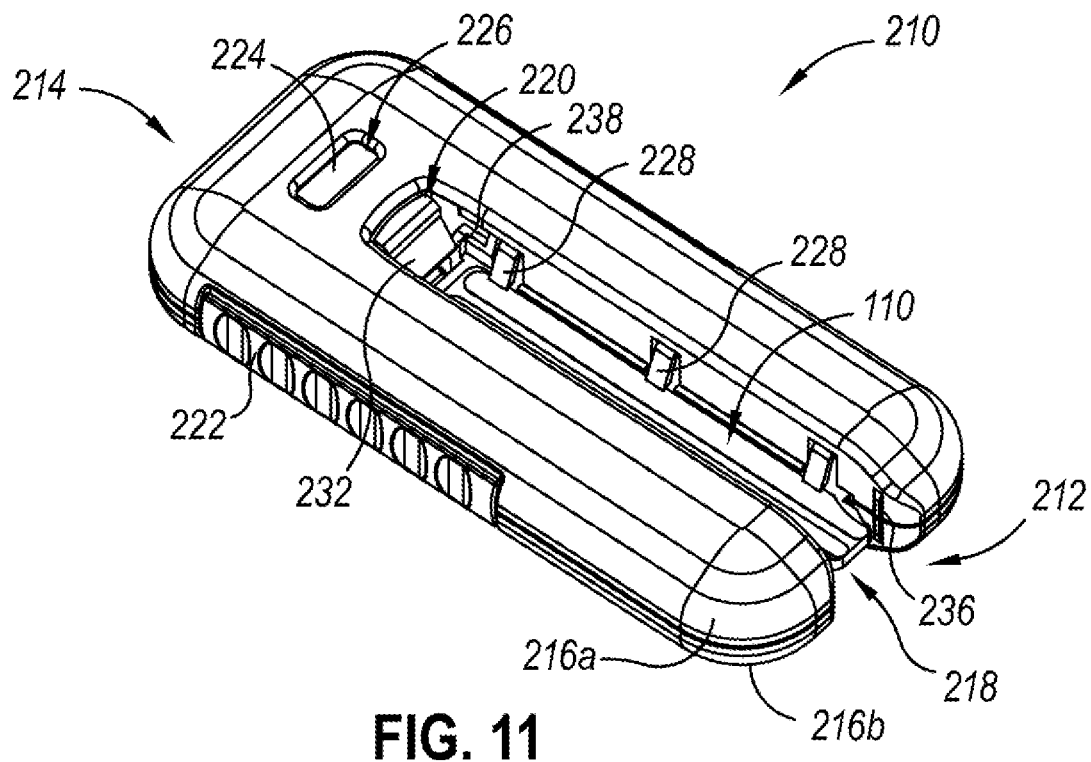
FIG. 11 depicts a perspective view of an exemplary buttress applier cartridge that may be used to carry and apply the buttress assemblies of FIG. 8.
Figure 12:
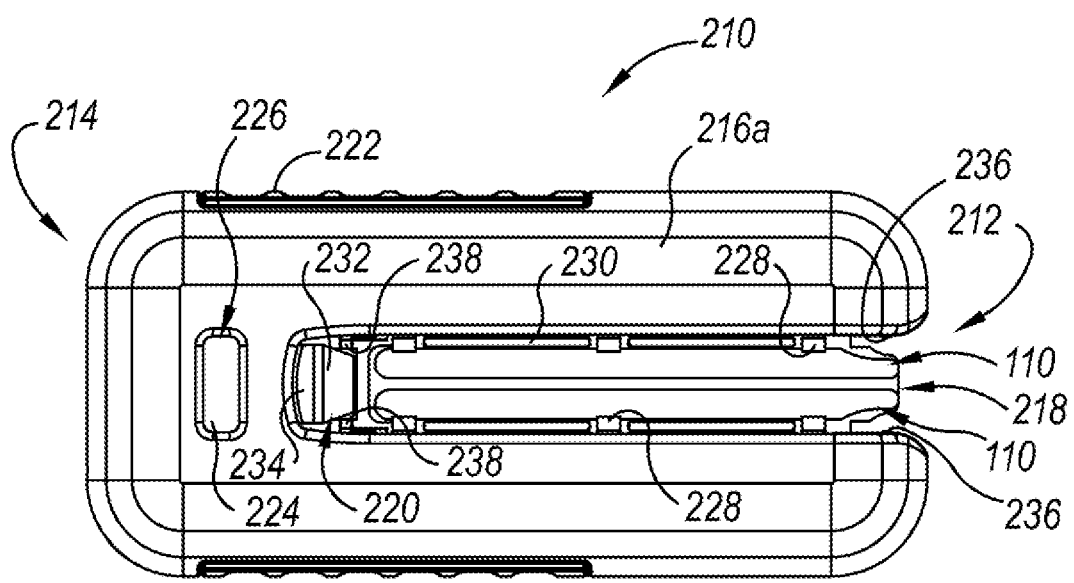
FIG. 12 depicts a top plan view of the buttress applier cartridge of FIG. 11.

Because end effector (12) of surgical instrument (10) may be actuated multiple times during a single surgical procedure, it may be desirable to enable an operator to repeatedly and easily load buttress assemblies (110, 112) onto end effector jaws (16, 18) during that single surgical procedure. FIGS. 11-13B show an exemplary buttress applier cartridge (210) (also referred to as a "buttress applicator") that may be used to support, protect, and apply adjunct material, such as buttress assemblies (110, 112), to end effector (12). As best seen in FIGS. 11-12, cartridge (210) of this example comprises an open end (212) and a closed end (214). Open end (212) is configured to receive end effector (12) as will be described in greater detail below. Cartridge (210) further includes a first housing (216a) and a second housing (216b), which each collectively generally define a "U" shape to present open end (212). A platform (218) and a sled retainer (220) are interposed between first and second housings (216a, 216b).

Platform (218) of the present example is configured to support a pair of buttress assemblies (110) on one side of platform (218) and another pair of buttress assemblies (112) on the other side of platform (218). Platform (218) is exposed in recesses that are formed between the prongs of the "U" configuration of first and second housings (216a, 216b). Each buttress assembly (110, 112) is provided in a respective pair of portions that are separated to avoid spanning across slots (42, 49) of anvil (18) and staple cartridge (37), respectively, though platform (218) may just as easily support wide versions of buttress assemblies (110, 112) that unitarily span across slots (42, 49) of anvil (18) and staple cartridge (37), respectively. More specifically, the outer edges of platform (218) include retention features (230) in the form of ridges that further engage first and second housings (216a, 216b) to prevent platform (218) from sliding relative to first and second housings (216a, 216b).

First and second housings (216a, 216b) include integral gripping features (222) and indicator plates (224) positioned to correspond with windows (226) formed in first and second housings (216a, 216b), such that indicator plates (224) are visible through windows (226) at different times. Arms (228) of the present example are configured to selectively secure buttress assemblies (110, 112) to platform (218). In the present example, arms (228) are resilient and are thus configured to resiliently bear against buttress assemblies (110, 112), thereby pinching buttress assemblies (110, 112) against platform (218). Buttress applier cartridge (210) includes a pair of tapered cam surfaces (232) and a respective pair of housing engagement features (234) positioned to engage corresponding surfaces of first and second housings (216a, 216b). First and second housings (216a, 216b) include proximal guide features (236) and distal guide features (238) configured to assist in providing proper alignment of end effector (40) with cartridge (210).

Figure 13A:
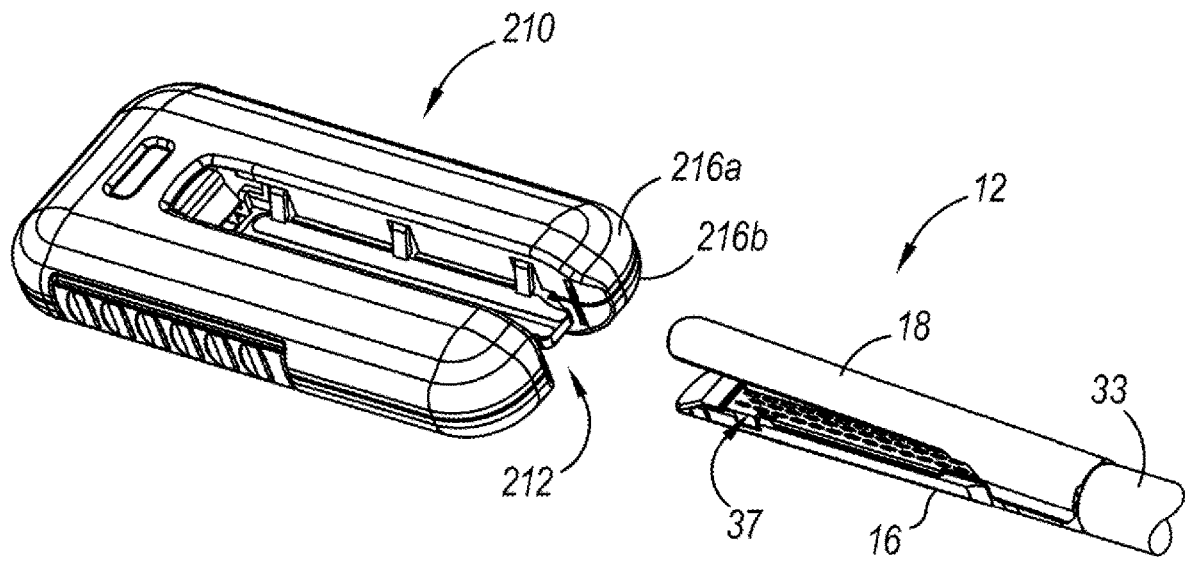
FIG. 13A depicts a perspective view of the end effector of FIG. 3 and the buttress applier cartridge of FIG. 11, showing the end effector and the buttress applier cartridge being aligned with one another.
Figure 13B:
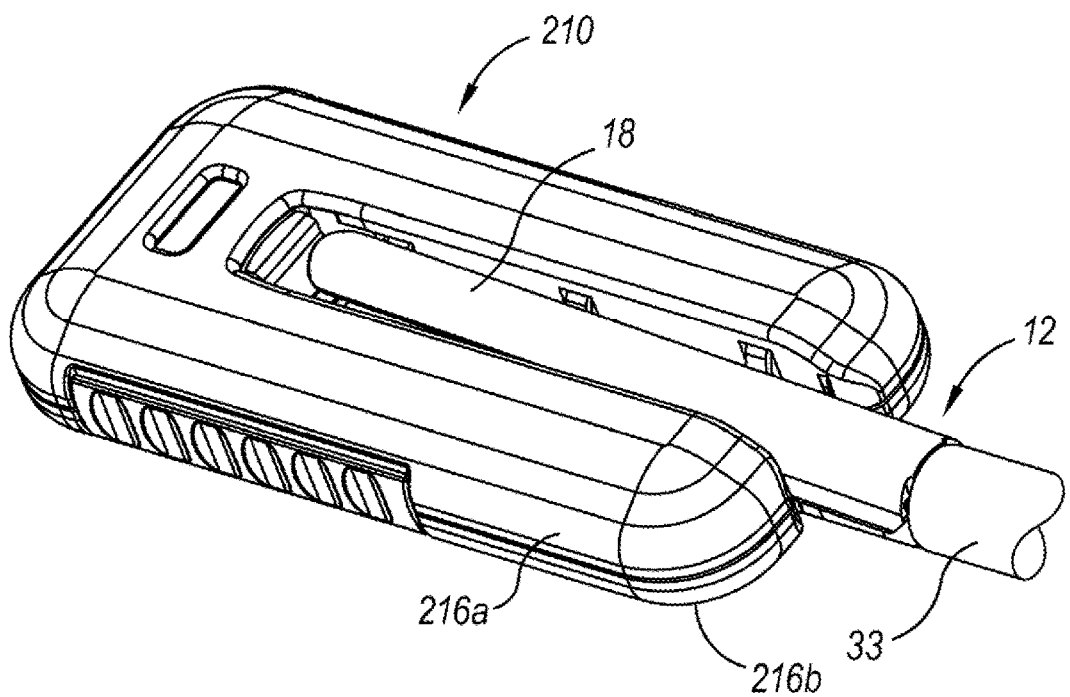
FIG. 13B depicts a perspective view of the end effector of FIG. 3 and the buttress applier cartridge of FIG. 11, with the end effectors jaws closed on a platform of the buttress applier cartridge.

FIG. 13A shows cartridge (210) in a configuration where retainer arms (228) are positioned to hold buttress assemblies (110, 112) against platform (218); while FIG. 13B shows cartridge (210) in a configuration where retainer arms (228) are positioned to release buttress assemblies (110, 112) from platform (218). While FIGS. 13A-13B only show buttress assembly (110) on platform (218), buttress assembly (112) would be retained on and released from platform (218) in an identical fashion. To use cartridge (210) to load end effector (12), the operator would first position cartridge (210) and end effector (12) such that end effector is aligned with open end (212) of cartridge (210) as shown in FIG. 13A. The operator would then advance end effector (12) distally, and/or advance cartridge (210) proximally, to position platform (218) and buttress assemblies (110, 112) between anvil (18) and staple cartridge (37) as shown in FIG. 13B. Closure trigger (26) of instrument (10) is then squeezed by the operator to close end effector jaws (16, 18) on platform (218), thereby adhesively attaching buttress assemblies (110, 112) to anvil (18) and staple cartridge (37), and simultaneously depressing cam surface (232). Depression of cam surface (232) actuates retainer arms (228) laterally outwardly to thereby release buttress assemblies (110, 112) from platform (218), such that end effector jaws (16, 18) may be disengaged from platform (218) while buttress assemblies (110, 112) remain adhered to anvil (18) and staple cartridge (37).

III. Exemplary Applicator Devices with Buttress Trimming Features

In some instances, it may be desirable to vary the length of a staple reinforcing adjunct element, such as for modifying the adjunct element to be compatible with an end effector jaw that may be incompatible with an initial length of the adjunct element. For example, an adjunct element may have an initial length (e.g., approximately 60 mm) for use with a first end effector jaw having a first jaw length (e.g., approximately 60 mm). In some instances, it may be desirable to shorten such an adjunct element to a predetermined subsequent length (e.g., approximately 45 mm) such that the adjunct element may be compatible with a second end effector jaw having a second jaw length (e.g., approximately 45 mm). Thus, it may be desirable to provide an applicator device that is configured to facilitate adjustment of the length of the adjunct element from the initial length to the predetermined subsequent length prior to application of the adjunct element to the end effector jaw. Each of the exemplary applicator devices described below provide such functionality.

It will be appreciated that any of the exemplary applicator devices described below may be configured to apply an adjunct element in the form of a buttress, such as buttresses (110, 112) described above, or a tissue thickness compensator, for example of the type disclosed in U.S. Pat. Pub. No. 2012/0080336, entitled "Staple Cartridge Comprising Staples Positioned Within A Compressible Portion Thereof," published Apr. 5, 2012 and now abandoned, the disclosure of which is incorporated by reference herein. Additionally, application of a staple reinforcement element to an end effector jaw may be achieved with adhesive features as described above and/or with mechanical coupling features, for example of the type disclosed in U.S. Pat. No. 7,665,646, entitled "Interlocking Buttress Material Retention System," issued Feb. 23, 2010, the disclosure of which is incorporated by reference herein. Furthermore, any of the exemplary applicator devices described below may be suitably constructed for a single use or for multiple uses.

A. Exemplary Buttress Applicator with Knife Grooves

Figure 14:
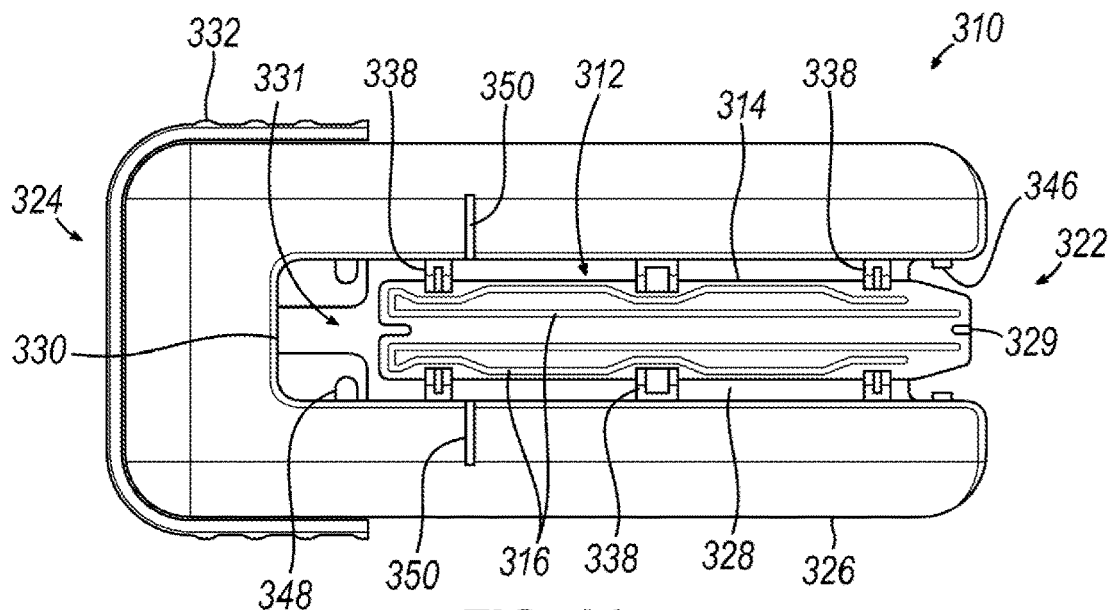
FIG. 14 depicts a top plan view of another exemplary buttress applicator for carrying and applying a buttress assembly, and having a laterally-opposed pair of knife grooves for facilitating trimming of the buttress assembly to a predetermined length.

FIG. 14 shows an exemplary buttress applicator (310) for applying at least one buttress assembly (312) to at least one jaw of an end effector, such as at least one jaw (16, 18) of end effector (12), and configured to facilitate adjustment of the length of buttress assembly (312). Buttress applicator (310) and buttress assembly (312) are similar to buttress applicator (210) and buttress assemblies (110, 112) described above, respectively, except as otherwise described below. In this regard, buttress assembly (312) of this example comprises a buttress body (314) and at least one adhesive bead (316) for adhering buttress body (314) to underside (124) of anvil (18) or to upper deck (72) of staple cartridge (37). In some versions, buttress assembly (312) may have an initial length of approximately 60 mm.

Buttress applicator (310) of this example comprises an open end (322) and a closed end (324). Open end (322) is configured to receive end effector (12) in a manner similar to that described above in connection with FIGS. 13A-13B. Buttress applicator (310) further includes at least one housing (326) which generally defines a "U" shape to present open end (322). A platform (328) extends longitudinally between proximal and distal ends (329, 330) and is exposed in one or more recesses (331) that are formed between the prongs of the "U" configuration of housing (326) and is configured to support buttress assembly (312) on an upper side of platform (328), though platform (328) may just as easily support another buttress assembly (312) on a lower side of platform (328). While buttress assembly (312) is illustrated as a relatively wide version that may unitarily span across slot (42) of anvil (18) or slot (49) of staple cartridge (37), buttress assembly (312) may be provided in a pair of portions that are separated to avoid spanning across either slot (42, 49). In any event, housing (326) includes integral gripping features (332), and a plurality of arms (338) are configured to resiliently bear against buttress assembly (312), thereby pinching buttress assembly (312) against platform (328) to selectively secure buttress assembly (312) to platform (328). Housing (326) also includes proximal guide features (346) and distal guide features (348) configured to assist in providing proper alignment of end effector (40) with buttress applicator (310).

Buttress applicator (310) of the present example further includes a buttress trimming feature in the form of a laterally-opposed pair of grooves (350) extending partially through housing (326) and configured to guide a blade of a cutting instrument, such as a knife or a scalpel (not shown), across buttress assembly (312) to thereby shorten buttress assembly (312) from the initial length to a predetermined subsequent length. More particularly, grooves (350) may guide such a blade to sever a scrap distal portion of buttress assembly (312) on the upper side of platform (328) from a desired proximal portion of buttress assembly (312) having the predetermined subsequent length. In this regard, grooves (350) each extend laterally outwardly from recess (331) and transversely downwardly from an upper surface of housing (326). In some versions, grooves (350) may each have a width in the longitudinal direction sufficient to slidably receive the blade. In addition, or alternatively, grooves (350) may each have a depth in the transverse direction relative to an upper surface of housing (326) generally equal to that of platform (328) such that a base surface of each groove (350) may be substantially flush with the upper surface of platform (328) to assist with maintaining the blade at a substantially constant height when guided across buttress assembly (312) by grooves (350). A cutting surface constructed of a material more durable than that of housing (326) may be embedded within housing (326) at or near the base surfaces of grooves (350) to inhibit the blade from scoring or otherwise cutting housing (326). For example, housing (326) may be constructed of silicone while such a cutting surface may be constructed of metal or any polymer having a greater durability than that of silicone. In some versions, such a cutting surface may extend across platform (328) to inhibit the blade from scoring or otherwise cutting platform (328).

Grooves (350) of the present example collectively define a cutting line that is generally perpendicular to the longitudinal direction and that is positioned at a predetermined distance from proximal end (329) of platform (328) corresponding to the predetermined subsequent length. For example, grooves (350) may be positioned approximately 45 mm from proximal end (329) such that the blade may shorten buttress assembly (312) to a predetermined subsequent length of approximately 45 mm when guided across buttress assembly (312) by grooves (350). It will be appreciated that grooves (350) may be positioned at any other suitable distance from proximal end (329) and/or may be suitably positioned relative to any other reference portion of buttress applicator (310) for facilitating shortening of buttress assembly (312). While a single pair of grooves (350) is shown for facilitating shortening of buttress assembly (312) to a single predetermined subsequent length, multiple pairs of grooves (350) may be provided along the length of platform (328) for facilitating shortening of buttress assembly (312) to any number of predetermined subsequent lengths. In any event, arms (338) may continue to secure the scrap distal portion of buttress assembly (312) to platform (328) after the desired proximal portion of buttress assembly (312) has been severed and applied to a corresponding end effector jaw (16, 18).

While grooves (350) are shown positioned on an upper side of housing (326), grooves (350) may additionally or alternatively be positioned on a lower side of housing (326), such as for guiding a blade across another buttress assembly (312) on the lower side of platform (328). Also, while grooves (350) are shown incorporated into buttress applicator (310) having the configuration described above, it will be appreciated that grooves (350) may be readily incorporated into a buttress applicator having any other suitable configuration, such as that described below in connection with FIGS. 18A-18C.

B. Exemplary Buttress Applicator with Scissor Slots

Figure 15:
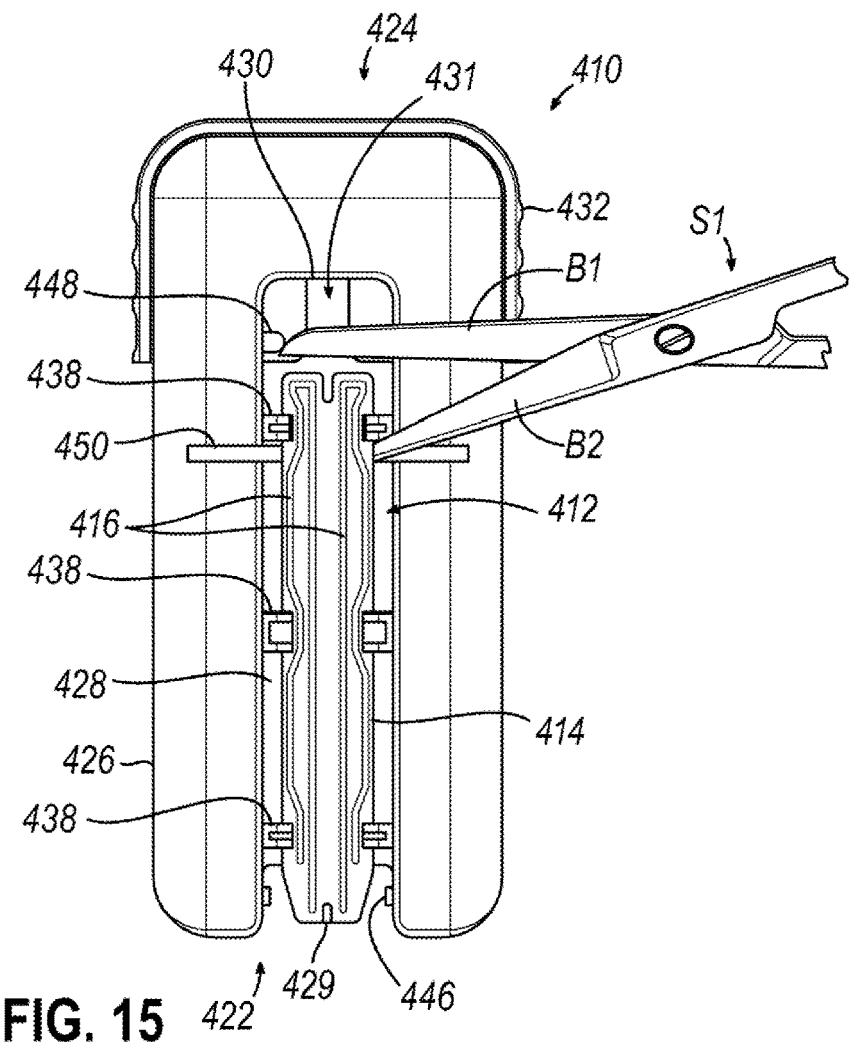
FIG. 15 depicts a top plan view of another exemplary buttress applicator for carrying and applying a buttress assembly, and having a scissor slot for facilitating trimming of the buttress assembly to a predetermined length.

FIG. 15 shows another exemplary buttress applicator (410) for applying at least one buttress assembly (412) to at least one jaw of an end effector, such as at least one jaw (16, 18) of end effector (12), and configured to facilitate adjustment of the length of buttress assembly (412). Buttress applicator (410) and buttress assembly (412) are similar to buttress applicator (210) and buttress assemblies (110, 112) described above, respectively, except as otherwise described below. In this regard, buttress assembly (412) of this example comprises a buttress body (414) and at least one adhesive bead (416) for adhering buttress body (414) to underside (124) of anvil (18) or to upper deck (72) of staple cartridge (37). In some versions, buttress assembly (412) may have an initial length of approximately 60 mm.

Buttress applicator (410) of this example comprises an open end (422) and a closed end (424). Open end (422) is configured to receive end effector (12) in a manner similar to that described above in connection with FIGS. 13A-13B. Buttress applicator (410) further includes at least one housing (426) which generally defines a "U" shape to present open end (422). A platform (428) extends longitudinally between proximal and distal ends (429, 430) and is exposed in one or more recesses (431) that are formed between the prongs of the "U" configuration of housing (426) and is configured to support buttress assembly (412) on an upper side of platform (428), though platform (428) may just as easily support another buttress assembly (412) on a lower side of platform (428). While buttress assembly (412) is illustrated as a relatively wide version that may unitarily span across slot (42) of anvil (18) or slot (49) of staple cartridge (37), buttress assembly (412) may be provided in a pair of portions that are separated to avoid spanning across either slot (42, 49). In any event, housing (426) includes integral gripping features (432), and a plurality of arms (438) are configured to resiliently bear against buttress assembly (412), thereby pinching buttress assembly (412) against platform (428) to selectively secure buttress assembly (412) to platform (428). Housing (426) also includes proximal guide features (446) and distal guide features (448) configured to assist in providing proper alignment of end effector (40) with buttress applicator (410).

Buttress applicator (410) of the present example further includes a buttress trimming feature in the form of a laterally-extending slot (450) extending through housing (426) and platform (428) and configured to guide one or more blades of a cutting instrument, such as one or more blades (B1, B2) of scissors (S1), across one or more buttress assemblies (412) to thereby shorten buttress assemblies (412) from the initial length to a predetermined subsequent length. More particularly, slot (450) may guide first blade (B1) to sever a scrap distal portion of buttress assembly (412) on the upper side of platform (428) from a desired proximal portion of buttress assembly (412) having the predetermined subsequent length, and slot (450) may also guide second blade (B2) to sever a scrap distal portion of another buttress assembly (412) on the lower side of platform (428) from a desired proximal portion of buttress assembly (412) having the predetermined subsequent length. In this regard, slot (450) extends laterally across platform (428) thereby bifurcating platform (428), and further extends laterally outwardly from recess (431) and transversely between upper and lower surfaces of housing (426). In some versions, slot (450) may have a width in the longitudinal direction sufficient to slidably receive one or both blades (B1, B2).

Slot (450) of the present example defines a cutting line that is generally perpendicular to the longitudinal direction and that is positioned at a predetermined distance from proximal end (429) of platform (428) corresponding to the predetermined subsequent length. For example, slot (450) may be positioned approximately 45 mm from proximal end (429) such that blade(s) (B1, B2) may shorten buttress assemblies (412) to a predetermined subsequent length of approximately 45 mm when guided across buttress assemblies (412) by slot (450). It will be appreciated that slot (450) may be positioned at any other suitable distance from proximal end (429) and/or may be suitably positioned relative to any other reference portion of buttress applicator (410) for facilitating shortening of buttress assemblies (412). While a single slot (450) is shown for facilitating shortening of buttress assemblies (412) to a single predetermined subsequent length, multiple slots (450) may be provided along the length of platform (428) for facilitating shortening of buttress assemblies (412) to any number of predetermined subsequent lengths. In any event, arms (438) may continue to secure the scrap distal portion of buttress assemblies (412) to platform (428) after the desired proximal portion(s) of buttress assemblies (412) has been severed and applied to a corresponding end effector jaw(s) (16, 18).

While slot (450) is shown bifurcating platform (428), slot (450) may alternatively be separated by platform (428) into a laterally-opposed pair of slots in an arrangement similar to that described above with respect to grooves (350). Also, while slot (450) is shown incorporated into buttress applicator (410) having the configuration described above, it will be appreciated that slot (450) may be readily incorporated into a buttress applicator having any other suitable configuration, such as that described below in connection with FIGS. 18A-18C.

C. Exemplary Buttress Applicator with Visual Cutting Indicia

FIG. 16 shows another exemplary buttress applicator (510) for applying at least one buttress assembly (512) to at least one jaw of an end effector, such as at least one jaw (16, 18) of end effector (12), and configured to facilitate adjustment of the length of buttress assembly (512). Buttress applicator (510) and buttress assembly (512) are similar to buttress applicator (210) and buttress assemblies (110, 112) described above, respectively, except as otherwise described below. In this regard, buttress assembly (512) of this example comprises a buttress body (514) and at least one adhesive bead (516) for adhering buttress body (514) to underside (124) of anvil (18) or to upper deck (72) of staple cartridge (37). In some versions, buttress assembly (512) may have an initial length of approximately 60 mm.

Buttress applicator (510) of this example comprises an open end (522) and a closed end (524). Open end (522) is configured to receive end effector (12) in a manner similar to that described above in connection with FIGS. 13A-13B. Buttress applicator (510) further includes at least one housing (526) which generally defines a "U" shape to present open end (522). A platform (528) extends longitudinally between proximal and distal ends (529, 530) and is exposed in one or more recesses (531) that are formed between the prongs of the "U" configuration of housing (526) and is configured to support buttress assembly (512) on an upper side of platform (528), though platform (528) may just as easily support another buttress assembly (512) on a lower side of platform (528). While buttress assembly (512) is illustrated as a relatively wide version that may unitarily span across slot (42) of anvil (18) or slot (49) of staple cartridge (37), buttress assembly (512) may be provided in a pair of portions that are separated to avoid spanning across either slot (42, 49). In any event, housing (526) includes integral gripping features (532), and a plurality of arms (538) are configured to resiliently bear against buttress assembly (512), thereby pinching buttress assembly (512) against platform (528) to selectively secure buttress assembly (512) to platform (528). Housing (526) also includes proximal guide features (546) and distal guide features (548) configured to assist in providing proper alignment of end effector (40) with buttress applicator (510).

Buttress applicator (510) of the present example further includes a buttress trimming feature in the form of a laterally-opposed pair of cutting indicia (550) provided on housing (526) and identifying a visible path for guiding a blade of a cutting instrument, such as a knife or a scalpel (not shown), across buttress assembly (512) to thereby shorten buttress assembly (512) from the initial length to a predetermined subsequent length. More particularly, indicia (550) may identify the path for guiding such a blade to sever a scrap distal portion of buttress assembly (512) on the upper side of platform (528) from a desired proximal portion of buttress assembly (512) having the predetermined subsequent length. In this regard, indicia (550) each include visually discernible arrows clearly identifying the path by pointing laterally inwardly toward each other. It will be appreciated that indicia (550) may be provided on housing (526) in any suitable manner, such as printing, molding, etching, or stamping, for example.

Indicia (550) of the present example collectively define a cutting line that is generally perpendicular to the longitudinal direction and that is positioned at a predetermined distance from proximal end (529) of platform (528) corresponding to the predetermined subsequent length. For example, indicia (550) may be positioned approximately 45 mm from proximal end (529) such that the blade may shorten buttress assembly (512) to a predetermined subsequent length of approximately 45 mm when guided across buttress assembly (512) along the path identified by indicia (550). It will be appreciated that indicia (550) may be positioned at any other suitable distance from proximal end (529) and/or may be suitably positioned relative to any other reference portion of buttress applicator (510) for facilitating shortening of buttress assembly (512). While a single pair of indicia (550) is shown for facilitating shortening of buttress assembly (512) to a single predetermined subsequent length, multiple pairs of indicia (550) may be provided along the length of platform (528) for facilitating shortening of buttress assembly (512) to any number of predetermined subsequent lengths. In any event, arms (538) may continue to secure the scrap distal portion of buttress assembly (512) to platform (528) after the desired proximal portion of buttress assembly (512) has been severed and applied to a corresponding end effector jaw (16, 18).

While indicia (550) are shown positioned on an upper side of housing (526), indicia (550) may additionally or alternatively be positioned on a lower side of housing (526), such as to identify a visible path for guiding a blade across another buttress assembly (512) on the lower side of platform (528). In some versions, indicia (550) may be provided in conjunction with grooves (350) and/or slot (450), such as in a hybrid configuration of buttress applicator (310) and buttress applicator (510) or in a hybrid configuration of buttress applicator (410) and buttress applicator (510). Also, while indicia (550) are shown incorporated into buttress applicator (510) having the configuration described above, it will be appreciated that indicia (550) may be readily incorporated into a buttress applicator having any other suitable configuration, such as that described below in connection with FIGS. 18A-18C.

D. Exemplary Buttress Applicator with Integrated Cutting Mechanism

FIGS. 17A-17B show another exemplary buttress applicator (610) for applying at least one buttress assembly (612) to at least one jaw of an end effector, such as at least one jaw (16, 18) of end effector (12), and configured to facilitate adjustment of the length of buttress assembly (612). Buttress applicator (610) and buttress assembly (612) are similar to buttress applicator (210) and buttress assemblies (110, 112) described above, respectively, except as otherwise described below. In this regard, buttress assembly (612) of this example comprises a buttress body (614) and at least one adhesive bead (616) for adhering buttress body (614) to underside (124) of anvil (18) or to upper deck (72) of staple cartridge (37). In some versions, buttress assembly (612) may have an initial length of approximately 60 mm.

Buttress applicator (610) of this example comprises an open end (not shown) and a closed end (624). The open end is configured to receive end effector (12) in a manner similar to that described above in connection with FIGS. 13A-13B. Buttress applicator (610) further includes at least one housing (626) which generally defines a "U" shape to present the open end. A platform (628) extends longitudinally between a proximal end (not shown) and a distal end (630) and is exposed in one or more recesses (631) that are formed between the prongs of the "U" configuration of housing (626) and is configured to support buttress assembly (612) on an upper side of platform (628), though platform (628) may just as easily support another buttress assembly (612) on a lower side of platform (628). While buttress assembly (612) is illustrated as a relatively wide version that may unitarily span across slot (42) of anvil (18) or slot (49) of staple cartridge (37), buttress assembly (612) may be provided in a pair of portions that are separated to avoid spanning across either slot (42, 49). In any event, housing (626) includes integral gripping features (632), and a plurality of arms (638) are configured to resiliently bear against buttress assembly (612), thereby pinching buttress assembly (612) against platform (628) to selectively secure buttress assembly (612) to platform (628). Housing (626) also includes proximal guide features (not shown) and distal guide features (648) configured to assist in providing proper alignment of end effector (40) with buttress applicator (610).

Buttress applicator (610) of the present example further includes a buttress trimming feature in the form of a laterally-opposed pair of cutting elements (650) slidably housed within respective grooves (652) extending partially through housing (626) and configured to guide cutting elements (650) across buttress assembly (612) to thereby shorten buttress assembly (612) from the initial length to a predetermined subsequent length. More particularly, grooves (652) may guide the respective cutting elements (650) to sever a scrap distal portion of buttress assembly (612) on the upper side of platform (628) from a desired proximal portion of buttress assembly (612) having the predetermined subsequent length. In this regard, grooves (652) each extend laterally outwardly from recess (631) and transversely downwardly from an upper surface of housing (626). As shown, grooves (652) each have a width in the longitudinal direction sufficient to slidably receive the respective cutting elements (650). In some versions, grooves (652) may each have a depth in the transverse direction relative to an upper surface of housing (626) generally equal to that of platform (628) such that a base surface of each groove (652) may be substantially flush with the upper surface of platform (628) to assist with maintaining the respective cutting elements (650) at a substantially constant height when guided across buttress assembly (612) by grooves (652). Such a configuration may also inhibit cutting elements (650) from scoring or otherwise cutting platform (328).

Cutting elements (650) each include a blade (654) extending laterally inwardly to a respective cutting edge (656), and each further include a manual actuator (658) extending transversely upwardly from a laterally outer end of the respective blade (654). Blades (654) may each be recessed below the upper surface of housing (626) while manual actuators (658) may each protrude at least slightly above the upper surface of housing (626) to enable an operator to grip manual actuators (658) for sliding cutting elements (650) laterally along the respective grooves (652) from a retracted state in which cutting edges (678) are spaced apart from buttress assembly (612) (FIG. 17A) to an extended state in which cutting edges (678) pass through buttress assembly (612). As shown, blades (654) may each have a length in the lateral direction sufficiently small to prevent cutting edges (656) from exiting the respective grooves (652) when in the retracted state and sufficiently great to permit cutting edges (656) to reach or slightly surpass a longitudinal centerline of platform (628) when in the extended state for ensuring full severing of buttress assembly (612). While a laterally-opposed pair of cutting elements (650) are shown for cooperating with each other to achieve full severing of buttress assembly (612), in some versions a single cutting element (650) may have a length in the lateral direction sufficiently great to permit such a single cutting element (650) to extend fully across platform (628) and thereby independently sever buttress assembly (612).

Grooves (652) of the present example collectively define a cutting line that is generally perpendicular to the longitudinal direction and that is positioned at a predetermined distance from the proximal end of platform (628) corresponding to the predetermined subsequent length. For example, grooves (652) may be positioned approximately 45 mm from the proximal end of platform (628) such that cutting elements (650) may shorten buttress assembly (612) to a predetermined subsequent length of approximately 45 mm when guided across buttress assembly (612) by grooves (652). It will be appreciated that grooves (652) may be positioned at any other suitable distance from the proximal end of platform (628) and/or may be suitably positioned relative to any other reference portion of buttress applicator (610) for facilitating shortening of buttress assembly (612). While a single pair of cutting elements (650) and respective grooves (652) are shown for facilitating shortening of buttress assembly (612) to a single predetermined subsequent length, multiple pairs of cutting elements (650) and respective grooves (652) may be provided along the length of platform (628) for facilitating shortening of buttress assembly (612) to any number of predetermined subsequent lengths. In any event, arms (638) may continue to secure the scrap distal portion of buttress assembly (612) to platform (628) after the desired proximal portion of buttress assembly (612) has been severed and applied to a corresponding end effector jaw (16, 18).

While cutting elements (650) and grooves (652) are shown positioned on an upper side of housing (626), cutting elements (650) and grooves (652) may additionally or alternatively be positioned on a lower side of housing (626), such as for guiding cutting elements (650) across another buttress assembly (612) on the lower side of platform (628). Also, while cutting elements (650) and grooves (652) are shown incorporated into buttress applicator (610) having the configuration described above, it will be appreciated that cutting elements (650) and grooves (652) may be readily incorporated into a buttress applicator having any other suitable configuration, such as that described below in connection with FIGS. 18A-18C.

E. Exemplary Alternative Buttress Applicator with Knife Grooves

Figure 18A:
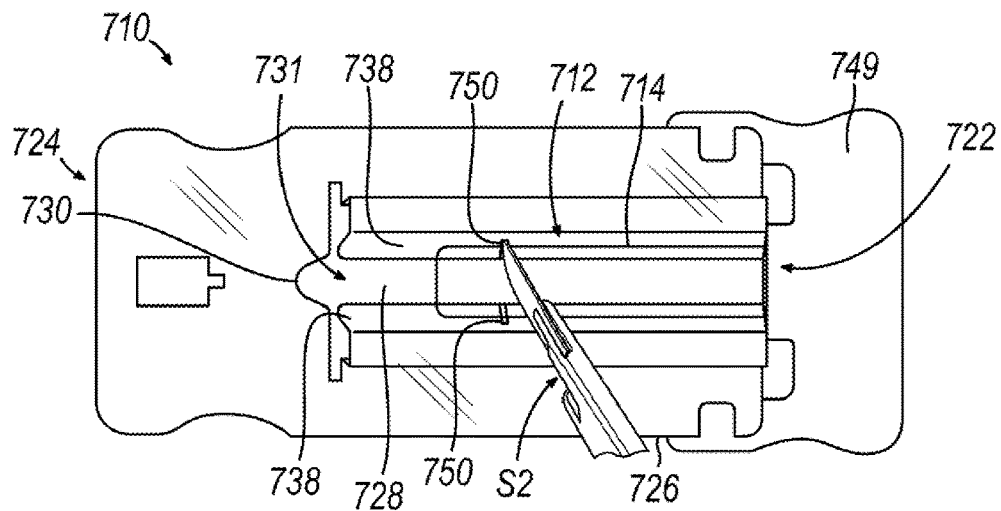
FIG. 18A depicts a top plan view of another exemplary buttress applicator for carrying and applying a buttress assembly, and having a laterally-opposed pair of knife grooves for facilitating trimming of the buttress assembly to a predetermined length, showing a scalpel trimming the buttress assembly.
Figure 18B:
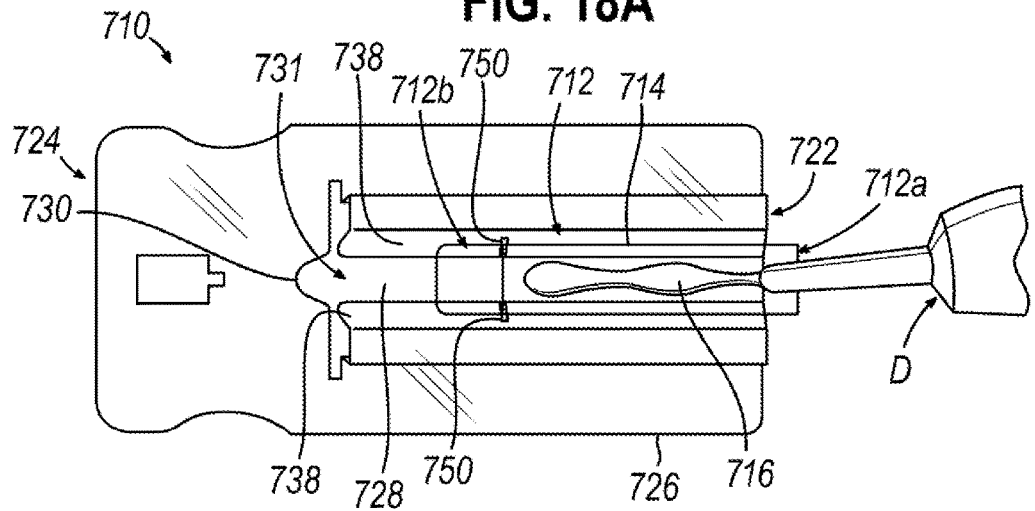
FIG. 18B depicts a top plan view of the buttress applicator of FIG. 18A, showing a dispenser depositing adhesive on a proximal portion of the buttress assembly.
Figure 18C:
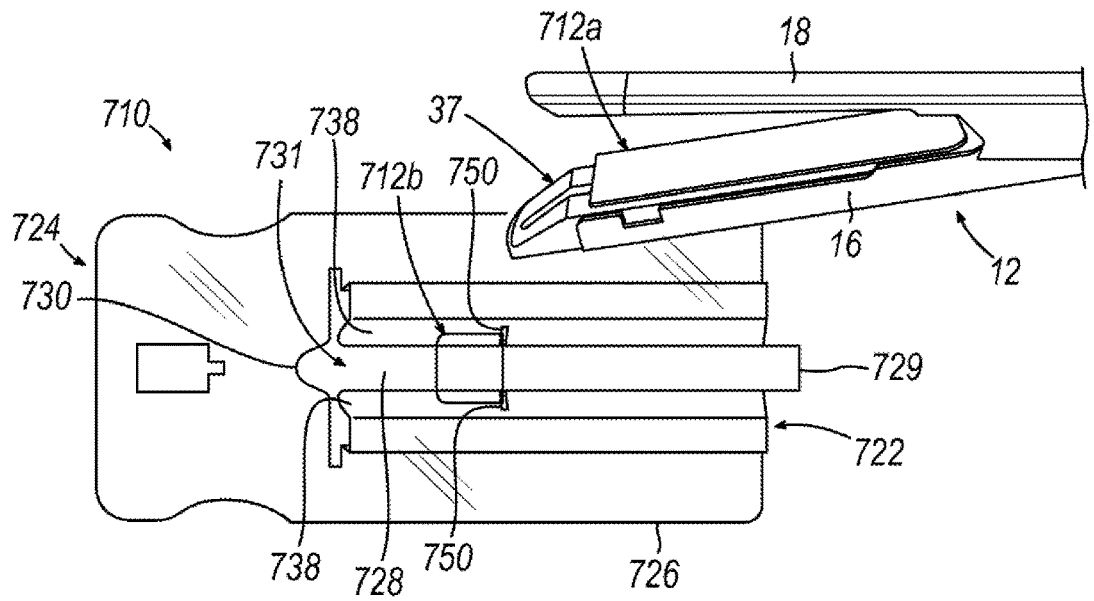
FIG. 18C depicts a top plan view of the buttress applicator of FIG. 18A, showing the proximal portion of the buttress assembly applied to an end effector jaw.

FIGS. 18A-18C show another exemplary buttress applicator (710) for applying at least one buttress assembly (712) to at least one jaw of an end effector, such as at least one jaw (16, 18) of end effector (12), and configured to facilitate adjustment of the length of buttress assembly (712). Buttress applicator (710) and buttress assembly (712) are similar to buttress applicator (210) and buttress assemblies (110, 112) described above, respectively, except as otherwise described below. In this regard, buttress assembly (712) of this example comprises a buttress body (714), which may be substantially transparent and/or translucent, and at least one adhesive bead (716) (FIG. 18B) for adhering buttress body (714) to underside (124) of anvil (18) or to upper deck (72) of staple cartridge (37). In some versions, adhesive bead (716) may be deposited onto at least a portion of buttress body (714) by the operator, as described in greater detail below. Buttress body (714) may comprise PERI-STRIPS DRY with VERITAS Collagen Matrix (PSDV) reinforcement material, by Baxter Healthcare Corporation of Deerfield, Ill., for example. In addition, or alternatively, buttress assembly (712) may have an initial length of approximately 60 mm.

Buttress applicator (710) of this example comprises an open end (722) and a closed end (724). Open end (722) is configured to receive end effector (12) in a manner similar to that described above in connection with FIGS. 13A-13B. Buttress applicator (710) further includes at least one housing (726) which generally defines a "U" shape to present open end (722). A platform (728) extends longitudinally between proximal and distal ends (729, 730) and is exposed in one or more recesses (731) that are formed between the prongs of the "U" configuration of housing (726) and is configured to support buttress assembly (712) on an upper side of platform (728), though platform (728) may just as easily support another buttress assembly (712) on a lower side of platform (728). While buttress assembly (712) is illustrated as a relatively wide version that may unitarily span across slot (42) of anvil (18) or slot (49) of staple cartridge (37), buttress assembly (712) may be provided in a pair of portions that are separated to avoid spanning across either slot (42, 49). In any event, a plurality of flanges (738) are configured to resiliently bear against buttress assembly (712), thereby pinching buttress assembly (712) against platform (728) to selectively secure buttress assembly (712) to platform (728). A buttress retainer (749) is removably coupled to open end (722).

Buttress applicator (710) of the present example further includes a buttress trimming feature in the form of a laterally-opposed pair of grooves (750) similar to grooves (350) described above in connection with FIG. 14. As shown, grooves (750) extend partially through housing (726) and/or flanges (738) and are configured to guide a blade of a scalpel (S2), across buttress assembly (712) to thereby shorten buttress assembly (712) from the initial length to a predetermined subsequent length. More particularly, grooves (750) may guide scalpel (S2) to sever a scrap distal portion (712b) of buttress assembly (712) on the upper side of platform (728) from a desired proximal portion (712a) of buttress assembly (712) having the predetermined subsequent length, such as approximately 45 mm, as shown in FIG. 18A. In some versions, buttress retainer (749) may be removed from open end (722) after scrap distal portion (712b) has been severed from desired proximal portion (712a), and adhesive bead (716) may be deposited onto desired proximal portion (712a) by the operator via an adhesive dispenser (D), as shown in FIG. 18B. The operator may then align an end effector, such as end effector (12) with open end (722), position platform (728) and buttress assembly (712) between anvil (18) and staple cartridge (37), close end effector jaws (16, 18) on platform (728), thereby adhesively attaching desired proximal portion (712a) of buttress assembly (712) to staple cartridge (37) (or anvil (18)), and disengage end effector jaws (16, 18) from platform (728) while desired proximal portion (712a) of buttress assembly (712) remains adhered to staple cartridge (37) (or anvil (18)), as shown in FIG. 18C. Flanges (738) may continue to secure scrap distal portion (712b) of buttress assembly (712) to platform (728) after desired proximal portion (712a) of buttress assembly (712) has been severed and applied to staple cartridge (37) (or anvil (18)).

While buttress applicator (710) is shown having a buttress trimming feature in the form of grooves (750), buttress applicator (710) may additionally or alternatively have any one or more of the other buttress trimming features described above in connection with FIGS. 15-17B. For example, buttress applicator (710) may include a slot similar to slot (450), indicia similar to indicia (550), and/or one or more cutting elements similar to cutting elements (650).

F. Exemplary Buttress Applicator Packaging with Integrated Cutting Mechanism

Figure 19A:
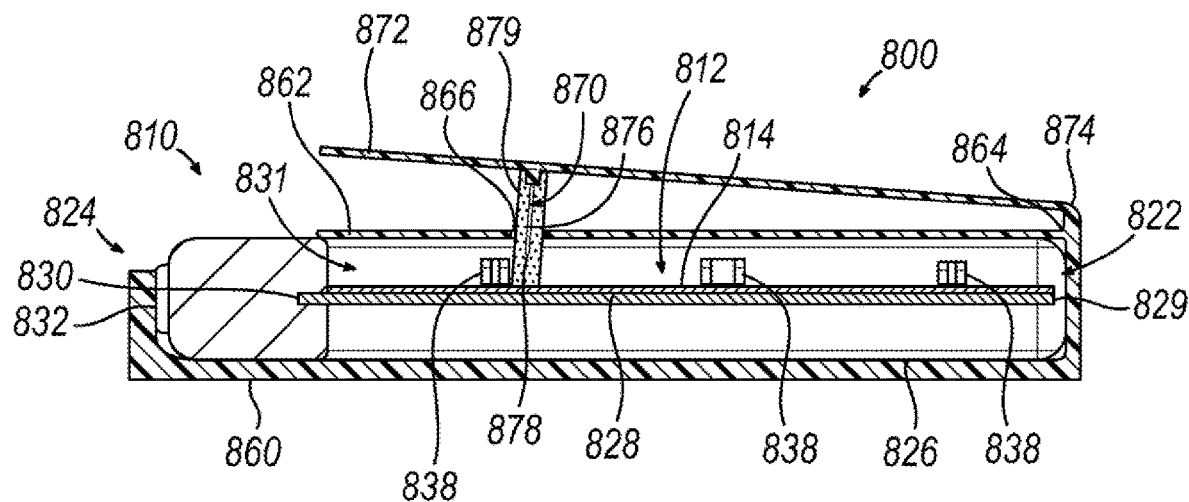
FIG. 19A depicts a side cross-sectional view of an exemplary tray containing a buttress applicator for carrying and applying a buttress assembly, and having a cutting element pivotable toward the buttress assembly for facilitating trimming of the buttress assembly to a predetermined length, showing the cutting element in a retracted state.
Figure 19B:
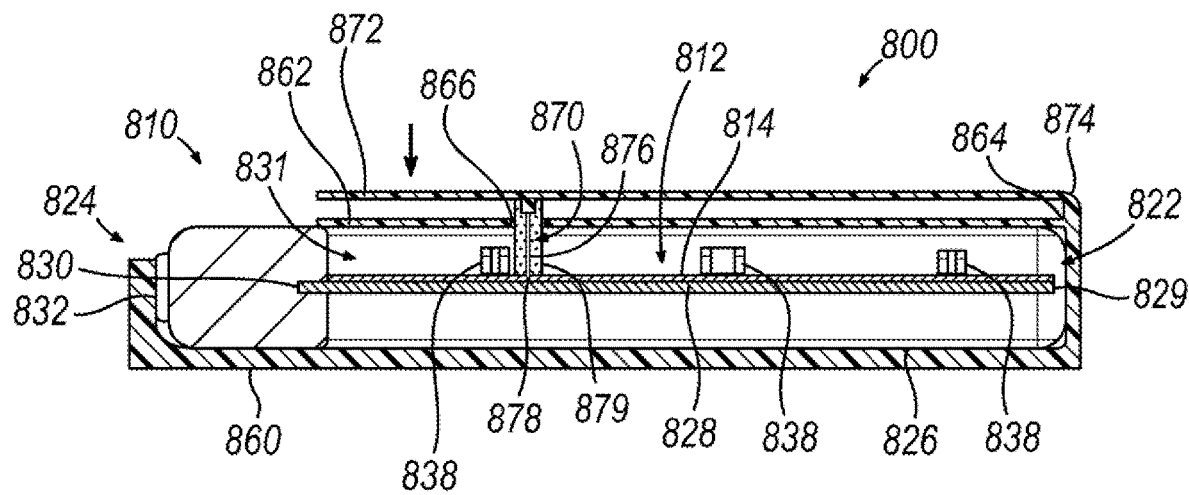
FIG. 19B depicts a side cross-sectional view of the tray of FIG. 19A, showing the cutting element in an extended state.

In some instances, it may be desirable to integrate a buttress trimming feature into the product packaging for a buttress applicator and the corresponding buttress assemblies. FIGS. 19A-19B show an exemplary packaging in the form of a tray (800) containing another buttress applicator (810) for applying at least one buttress assembly (812) to at least one jaw of an end effector, such as at least one jaw (16, 18) of end effector (12). Tray (800) is configured to facilitate adjustment of the length of buttress assembly (812). Buttress applicator (810) and buttress assembly (812) are similar to buttress applicator (210) and buttress assemblies (110, 112) described above, respectively, except as otherwise described below. In this regard, buttress assembly (812) of this example comprises a buttress body (814) and at least one adhesive bead or other type of adhesive layer (not shown) for adhering buttress body (814) to underside (124) of anvil (18) or to upper deck (72) of staple cartridge (37). In some versions, buttress assembly (812) may have an initial length of approximately 60 mm.

Buttress applicator (810) of this example comprises an open end (822) and a closed end (824). Open end (822) is configured to receive end effector (12) in a manner similar to that described above in connection with FIGS. 13A-13B. Buttress applicator (810) further includes at least one housing (826) which generally defines a "U" shape to present open end (822). A platform (828) extends longitudinally between proximal and distal ends (829, 830) and is exposed in one or more recesses (831) that are formed between the prongs of the "U" configuration of housing (826) and is configured to support buttress assembly (812) on an upper side of platform (828), though platform (828) may just as easily support another buttress assembly (812) on a lower side of platform (828). In any event, housing (826) includes integral gripping features (832), and a plurality of arms (838) are configured to resiliently bear against buttress assembly (812), thereby pinching buttress assembly (812) against platform (828) to selectively secure buttress assembly (812) to platform (828).

Tray (800) comprises a base (860), a first flap (862), and a first living hinge (864) connecting first flap (862) with base (860). Base (860) of tray (800) is configured to selectively retain applicator (810). First flap (862) is rotatable from a closed position, in which first flap (862) at least partially covers applicator (810) when applicator (810) is retained within base (860) as shown in FIGS. 19A-19B, to an open position, in which first flap (862) reveals applicator (810) such that it may be removed from tray (800). In the example shown, an aperture (866) extends through a portion of first flap (862) generally near distal end (830) of platform (828), the purpose of which is described below.

Tray (800) of the present example further includes a buttress trimming feature in the form of a cutting element (870) pivotably coupled to base (860) via a second flap (872) and a second living hinge (874) connecting second flap (872) with base (860) above first flap (862). Aperture (866) is configured to guide cutting element (870) through first flap (862) toward buttress assembly (812) to thereby shorten buttress assembly (812) from the initial length to a predetermined subsequent length. More particularly, aperture (866) may guide cutting element (870) to sever a scrap distal portion of buttress assembly (812) on the upper side of platform (828) from a desired proximal portion of buttress assembly (812) having the predetermined subsequent length. In this regard, aperture (866) extends transversely through first flap (862) along a pivot path of cutting element (870).

Cutting element (870) includes a blade (876) extending transversely downwardly from second flap (872) to a cutting edge (878). Second flap (872) may be pressed transversely downwardly by the operator for pushed cutting element (870) downwardly through aperture (866) from a retracted state in which cutting edge (878) is spaced apart from buttress assembly (812) (FIG. 19A) to an extended state in which cutting edge (878) passes through buttress assembly (812) (FIG. 19B). As shown, blade (876) may have a length in the transverse direction sufficiently small to prevent cutting edge (878) from contacting buttress assembly (812) when in the retracted state and sufficiently great to permit cutting edges (656) to pass entirely through buttress assembly (812) when in the extended state for ensuring full severing of buttress assembly (612). In the example shown, a compressible foam block (879) is positioned within aperture (866) for housing at least a portion of blade (876) and/or cutting edge (878) when cutting element (870) is in the retracted state, while permitting cutting edge (878) to exit foam block (879) when cutting element (870) is in the extended state such as by compressing and/or piercing through foam block (879). In some versions, a recess (not shown) may be provided in the upper side of platform (828) for receiving cutting edge (878) when in the extended state to inhibit cutting element (870) from scoring or otherwise cutting platform (828).

Cutting edge (878) of the present example defines a cutting line that is generally perpendicular to the longitudinal direction and that is positioned at a predetermined distance from proximal end (829) of platform (828) corresponding to the predetermined subsequent length, at least when cutting element (870) is in the extended state. For example, cutting edge (878) may be positioned approximately 45 mm from proximal end (829) such that cutting element (852) may shorten buttress assembly (812) to a predetermined subsequent length of approximately 45 mm when in the extended state. It will be appreciated that cutting edge (878) may be positioned at any other suitable distance from proximal end (829) and/or may be suitably positioned relative to any other reference portion of buttress applicator (810) or tray (800) for facilitating shortening of buttress assembly (812). In any event, arms (838) may continue to secure the scrap distal portion of buttress assembly (812) to platform (828) after the desired proximal portion of buttress assembly (812) has been severed and applied to a corresponding end effector jaw (16, 18).

Tray (800) may be further constructed and operable in accordance with any one or more teachings of U.S. Pat. Pub. No. 2020/0205824, entitled "Packaging for Surgical Stapler Buttress," published Jul. 2, 2020, the disclosure of which is incorporated by reference herein.

IV. Exemplary Buttress Assemblies with Variable Length Features

As described above, it may be desirable to vary the length of a staple reinforcing adjunct element, such as for modifying the adjunct element to be compatible with an end effector jaw that may be incompatible with an initial length of the adjunct element. For example, an adjunct element may have an initial length (e.g., approximately 60 mm) for use with a first end effector jaw having a first jaw length (e.g., approximately 60 mm). In some instances, it may be desirable to shorten such an adjunct element to a predetermined subsequent length (e.g., approximately 45 mm) such that the adjunct element may be compatible with a second end effector jaw having a second jaw length (e.g., approximately 45 mm). Thus, it may be desirable to provide an adjunct element with one or more variable length features to facilitate adjustment of the length of the adjunct element from the initial length to the predetermined subsequent length prior to or after application of the adjunct element to the end effector jaw. Each of the exemplary buttress assemblies described below provide such functionality.

A. Exemplary Buttress Assembly with Notches

Figure 20:
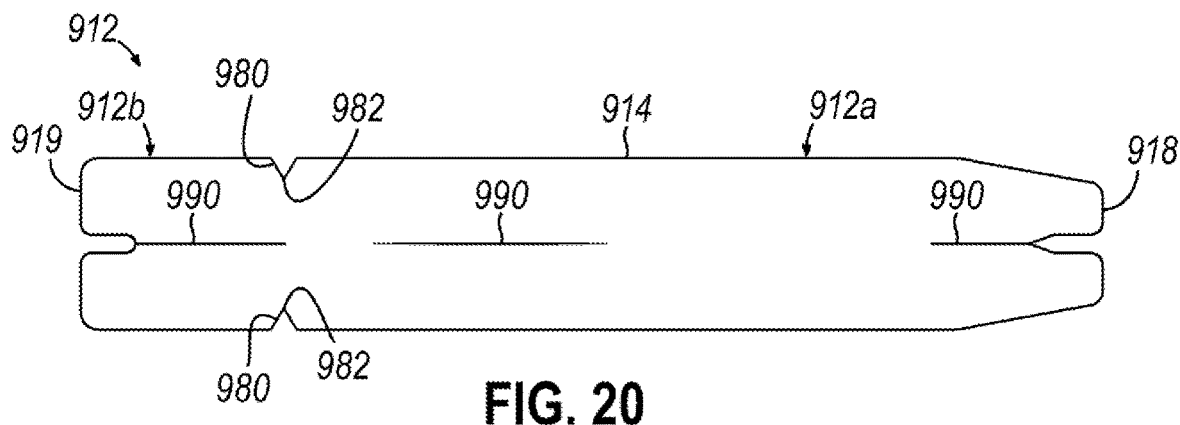
FIG. 20 depicts a top plan view of another exemplary buttress assembly having a laterally-opposed pair of notches for facilitating adjustment of the buttress assembly to a predetermined length.

FIG. 20 shows an exemplary adjunct element in the form of a buttress assembly (912) having separable proximal and distal portions (912a, 912b) configured to facilitate adjustment of the length of buttress assembly (912). Buttress assembly (912) is similar to buttress assemblies (110, 112) described above, except as otherwise described below. In this regard, buttress assembly (912) of this example comprises a buttress body (914) extending longitudinally between proximal and distal ends (918, 919). Buttress assembly (912) may also comprise at least one adhesive bead or other type of adhesive layer (not shown) for adhering buttress body (914) to underside (124) of anvil (18) or to upper deck (72) of staple cartridge (37). In some versions, buttress assembly (912) may have an initial length of approximately 60 mm.

Buttress assembly (912) of the present example further includes a variable length feature in the form of a laterally-opposed pair of notches (980) extending partially through buttress body (914) and identifying a visible path for guiding a blade of a cutting instrument, such as a knife or a scalpel (not shown), across buttress assembly (912) to thereby shorten buttress assembly (912) from the initial length to a predetermined subsequent length. More particularly, notches (980) may identify the path for guiding such a blade to sever a scrap distal portion (912b) of buttress assembly (912) from a desired proximal portion (912a) of buttress assembly (912) having the predetermined subsequent length. In this regard, notches (980) are each generally triangular and extend laterally inwardly from respective lateral edges of buttress body (914) to define respective apexes (982) clearly identifying the path by pointing laterally inwardly toward each other.

Notches (980) of the present example and, more particularly, apexes (982), collectively define a cutting line that is generally perpendicular to the longitudinal direction and that is positioned at a predetermined distance from proximal end (918) of buttress body (914) corresponding to the predetermined subsequent length, such that the cutting line delineates proximal and distal portions (912a, 912b) of buttress assembly (912). For example, apexes (982) of notches (980) may be positioned approximately 45 mm from proximal end (918) such that the blade may shorten buttress assembly (912) to a predetermined subsequent length of approximately 45 mm when guided across buttress assembly (912) along the path identified by apexes (982) of notches (980). It will be appreciated that apexes (982) of notches (980) may be positioned at any other suitable distance from proximal end (918) and/or may be suitably positioned relative to any other reference portion of buttress assembly (912) for facilitating shortening of buttress assembly (912). In some versions, the position of notches (980) may be fine-tuned to prevent a staple leg from passing through either notch (980) in operations where buttress assembly (1312) is used while maintaining the initial length of buttress assembly (1312). While a single pair of notches (980) is shown for facilitating shortening of buttress assembly (912) to a single predetermined subsequent length, multiple pairs of notches (980) may be provided along the length of buttress body (914) for facilitating shortening of buttress assembly (912) to any number of predetermined subsequent lengths.

While notches (980) are shown incorporated into buttress assembly (912) having the configuration described above, it will be appreciated that notches (980) may be readily incorporated into a buttress assembly having any other suitable configuration, such as a generally rectangular configuration similar to that shown in FIGS. 18A-18C.

Buttress assembly (912) also comprises multiple slits (990) that extend longitudinally along buttress body (914) to generally divide buttress body (914) into two equal sections. Referring to FIG. 10, when buttress assembly (912) is used with end effector (12) in a cutting and stapling procedure, cutting edge (48) of firing beam (14) will travel longitudinally through end effector (12) to cut clamped tissue and at the same time cut buttress body (914) of buttress assembly (912) along slits (990). This creates the cut and stapled site as illustrated in FIG. 10. Slits (990) act as precuts in buttress body (914) such that during a cutting and stapling action, buttress body (914) offers less resistance to being cut, which promotes buttress body (914) remaining properly placed relative to the surgically cut and stapled site, instead of buttress body (914) being pushed longitudinally by cutting edge (48) and bunching. While the present example uses slits (990) to precut and promote ease of cutting buttress body (914), in view of the teachings herein, other techniques and precut geometries can be used and will be apparent to those of ordinary skill in the art.

B. Exemplary Buttress Assembly with Printed Visual Cutting Indicia

Figure 21:
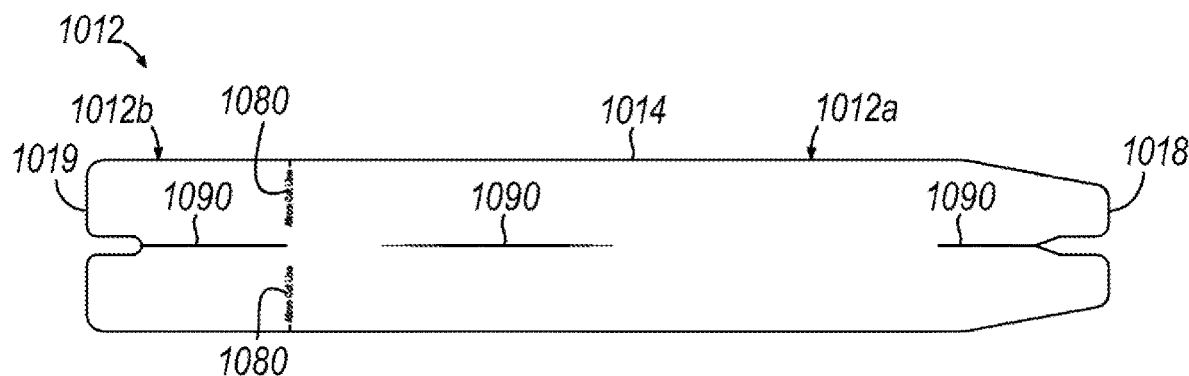
FIG. 21 depicts a top plan view of another exemplary buttress assembly having a laterally-opposed pair of printed visual indicia for facilitating adjustment of the buttress assembly to a predetermined length.

FIG. 21 shows another exemplary adjunct element in the form of a buttress assembly (1012) having separable proximal and distal portions (1012a, 1012b) configured to facilitate adjustment of the length of buttress assembly (1012). Buttress assembly (1012) is similar to buttress assemblies (110, 112) described above, except as otherwise described below. In this regard, buttress assembly (1012) of this example comprises a buttress body (1014) extending longitudinally between proximal and distal ends (1018, 1019). Buttress assembly (1012) may also comprise at least one adhesive bead or other type of adhesive layer (not shown) for adhering buttress body (1014) to underside (124) of anvil (18) or to upper deck (72) of staple cartridge (37). In some versions, buttress assembly (1012) may have an initial length of approximately 60 mm.

Buttress assembly (1012) of the present example further includes a variable length feature in the form of a laterally-opposed pair of cutting indicia (1080) provided on buttress body (1014) and identifying a visible path for guiding a blade of a cutting instrument, such as a knife or a scalpel (not shown), across buttress assembly (1012) to thereby shorten buttress assembly (1012) from the initial length to a predetermined subsequent length. More particularly, indicia (1080) may identify the path for guiding such a blade to sever a scrap distal portion (1012b) of buttress assembly (1012) from a desired proximal portion (1012a) of buttress assembly (1012) having the predetermined subsequent length. In this regard, indicia (1080) each include visually discernible text clearly identifying the path by stating "45 mm cut line" along the path. It will be appreciated that indicia (1080) may be provided on buttress body (1014) in any suitable manner, such as printing/inking, for example.

Indicia (1080) of the present example collectively define a cutting line that is generally perpendicular to the longitudinal direction and that is positioned at a predetermined distance from proximal end (1018) of buttress body (1014) corresponding to the predetermined subsequent length, such that the cutting line delineates proximal and distal portions (1012a, 1012b) of buttress assembly (1012). For example, indicia (1080) may be positioned approximately 45 mm from proximal end (1018) such that the blade may shorten buttress assembly (1012) to a predetermined subsequent length of approximately 45 mm when guided across buttress assembly (1012) along the path identified by indicia (1080). It will be appreciated that indicia (1080) may be positioned at any other suitable distance from proximal end (1018) and/or may be suitably positioned relative to any other reference portion of buttress assembly (1012) for facilitating shortening of buttress assembly (1012). While a single pair of indicia (1080) is shown for facilitating shortening of buttress assembly (1012) to a single predetermined subsequent length, multiple pairs of indicia (1080) may be provided along the length of buttress body (1014) for facilitating shortening of buttress assembly (1012) to any number of predetermined subsequent lengths.

While indicia (1080) are shown incorporated into buttress assembly (1012) having the configuration described above, it will be appreciated that indicia (1080) may be readily incorporated into a buttress assembly having any other suitable configuration, such as a generally rectangular configuration similar to that shown in FIGS. 18A-18C.

Buttress assembly (1012) also comprises multiple slits (1090) that extend longitudinally along buttress body (1014) to generally divide buttress body (1014) into two equal sections. Referring to FIG. 10, when buttress assembly (1012) is used with end effector (12) in a cutting and stapling procedure, cutting edge (48) of firing beam (14) will travel longitudinally through end effector (12) to cut clamped tissue and at the same time cut buttress body (1014) of buttress assembly (1012) along slits (1090). This creates the cut and stapled site as illustrated in FIG. 10. Slits (1090) act as precuts in buttress body (1014) such that during a cutting and stapling action, buttress body (1014) offers less resistance to being cut, which promotes buttress body (1014) remaining properly placed relative to the surgically cut and stapled site, instead of buttress body (1014) being pushed longitudinally by cutting edge (48) and bunching. While the present example uses slits (1090) to precut and promote ease of cutting buttress body (1014), in view of the teachings herein, other techniques and precut geometries can be used and will be apparent to those of ordinary skill in the art.

Figure 22:
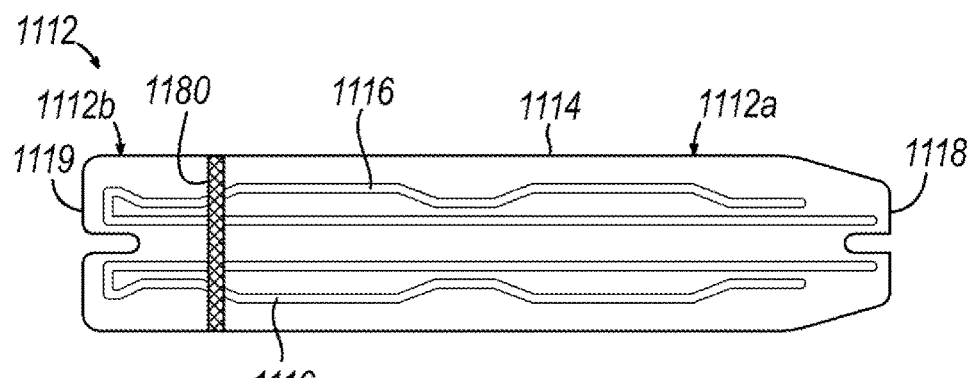
FIG. 22 depicts a top plan view of another exemplary buttress assembly having a laterally-opposed pair of visual indicia formed by a material change for facilitating adjustment of the buttress assembly to a predetermined length.

C. Exemplary Buttress Assembly with Visual Cutting Indicia Provided via Change in Material FIG. 22 shows another exemplary adjunct element in the form of a buttress assembly (1112) having separable proximal and distal portions (1112a, 1112b) configured to facilitate adjustment of the length of buttress assembly (1112). Buttress assembly (1112) is similar to buttress assemblies (110, 112) described above, except as otherwise described below. In this regard, buttress assembly (1112) of this example comprises a buttress body (1114) extending longitudinally between proximal and distal ends (1118, 1119). Buttress assembly (1112) may also comprise at least one adhesive bead (1116) for adhering buttress body (1114) to underside (124) of anvil (18) or to upper deck (72) of staple cartridge (37). In some versions, buttress assembly (1112) may have an initial length of approximately 60 mm.

Buttress assembly (1112) of the present example further includes a variable length feature in the form of a cutting indicia (1180) integrated into buttress body (1114) and identifying a visible path for guiding a blade of a cutting instrument, such as a knife or a scalpel (not shown), across buttress assembly (1112) to thereby shorten buttress assembly (1112) from the initial length to a predetermined subsequent length. More particularly, indicia (1180) may identify the path for guiding such a blade to sever a scrap distal portion (1112b) of buttress assembly (1112) from a desired proximal portion (1112a) of buttress assembly (1112) having the predetermined subsequent length. In this regard, indicia (1180) may include a visually discernible color clearly identifying the path by differing from a color of the remainder of buttress body (1114). It will be appreciated that indicia (1180) may be integrated into buttress body (1114) in any suitable manner, such as by forming the portion of buttress body (1114) defining indicia (1180) from a material different from that used to form the remainder of buttress body (1114), for example.

Indicia (1180) of the present example defines a cutting line that is generally perpendicular to the longitudinal direction and that is positioned at a predetermined distance from proximal end (1118) of buttress body (1114) corresponding to the predetermined subsequent length, such that the cutting line delineates proximal and distal portions (1112a, 1112b) of buttress assembly (1112). For example, indicia (1180) may be positioned approximately 45 mm from proximal end (1118) such that the blade may shorten buttress assembly (1112) to a predetermined subsequent length of approximately 45 mm when guided across buttress assembly (1112) along the path identified by indicia (1180). It will be appreciated that indicia (1180) may be positioned at any other suitable distance from proximal end (1118) and/or may be suitably positioned relative to any other reference portion of buttress assembly (1112) for facilitating shortening of buttress assembly (1112). While a single indicia (1180) is shown for facilitating shortening of buttress assembly (1112) to a single predetermined subsequent length, multiple indicia (1180) may be provided along the length of buttress body (1114) for facilitating shortening of buttress assembly (1112) to any number of predetermined subsequent lengths.

While indicia (1180) is shown incorporated into buttress assembly (1112) having the configuration described above, it will be appreciated that indicia (1180) may be readily incorporated into a buttress assembly having any other suitable configuration, such as a generally rectangular configuration similar to that shown in FIGS. 18A-18C.

Figure 23:
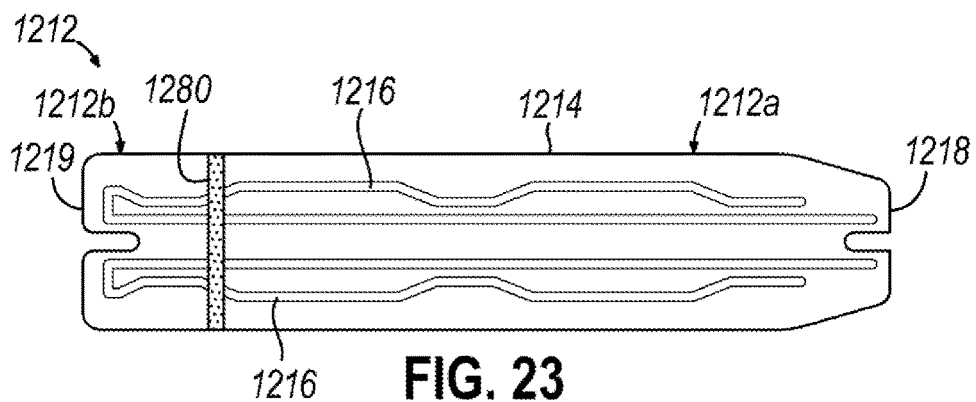
FIG. 23 depicts a top plan view of another exemplary buttress assembly having a laterally-opposed pair of visual indicia formed by a manufacturing process for facilitating adjustment of the buttress assembly to a predetermined length.

D. Exemplary Buttress Assembly with Visual Cutting Indicia Provided Via Manufacturing Process FIG. 23 shows another exemplary adjunct element in the form of a buttress assembly (1212) having separable proximal and distal portions (1212a, 1212b) configured to facilitate adjustment of the length of buttress assembly (1212). Buttress assembly (1212) is similar to buttress assemblies (110, 112) described above, except as otherwise described below. In this regard, buttress assembly (1212) of this example comprises a buttress body (1214) extending longitudinally between proximal and distal ends (1218, 1219). Buttress assembly (1212) may also comprise at least one adhesive bead (1216) for adhering buttress body (1214) to underside (124) of anvil (18) or to upper deck (72) of staple cartridge (37). In some versions, buttress assembly (1212) may have an initial length of approximately 60 mm.

Buttress assembly (1212) of the present example further includes a variable length feature in the form of a cutting indicia (1280) integrated into buttress body (1214) and identifying a visible path for guiding a blade of a cutting instrument, such as a knife or a scalpel (not shown), across buttress assembly (1212) to thereby shorten buttress assembly (1212) from the initial length to a predetermined subsequent length. More particularly, indicia (1280) may identify the path for guiding such a blade to sever a scrap distal portion (1212b) of buttress assembly (1212) from a desired proximal portion (1212a) of buttress assembly (1212) having the predetermined subsequent length. In this regard, indicia (1280) may include a visually discernible color clearly identifying the path by differing from a color of the remainder of buttress body (1214). It will be appreciated that indicia (1280) may be integrated into buttress body (1214)

in any suitable manner, such as by subjecting the portion of buttress body (1214) defining indicia (1280) to a color-altering manufacturing process (e.g., UV, chemical, and/or electrical etching) without subjecting the remainder of buttress body (1214) to the color-altering manufacturing process, for example.

Indicia (1280) of the present example defines a cutting line that is generally perpendicular to the longitudinal direction and that is positioned at a predetermined distance from proximal end (1218) of buttress body (1214) corresponding to the predetermined subsequent length, such that the cutting line delineates proximal and distal portions (1212a, 1212b) of buttress assembly (1212). For example, indicia (1280) may be positioned approximately 45 mm from proximal end (1218) such that the blade may shorten buttress assembly (1212) to a predetermined subsequent length of approximately 45 mm when guided across buttress assembly (1212) along the path identified by indicia (1280). It will be appreciated that indicia (1280) may be positioned at any other suitable distance from proximal end (1218) and/or may be suitably positioned relative to any other reference portion of buttress assembly (1212) for facilitating shortening of buttress assembly (1212). While a single indicia (1280) is shown for facilitating shortening of buttress assembly (1212) to a single predetermined subsequent length, multiple indicia (1280) may be provided along the length of buttress body (1214) for facilitating shortening of buttress assembly (1212) to any number of predetermined subsequent lengths.

While indicia (1280) is shown incorporated into buttress assembly (1212) having the configuration described above, it will be appreciated that indicia (1280) may be readily incorporated into a buttress assembly having any other suitable configuration, such as a generally rectangular configuration similar to that shown in FIGS. 18A-18C.

E. Exemplary Buttress Assembly with Purse String Attachment

Figure 24:
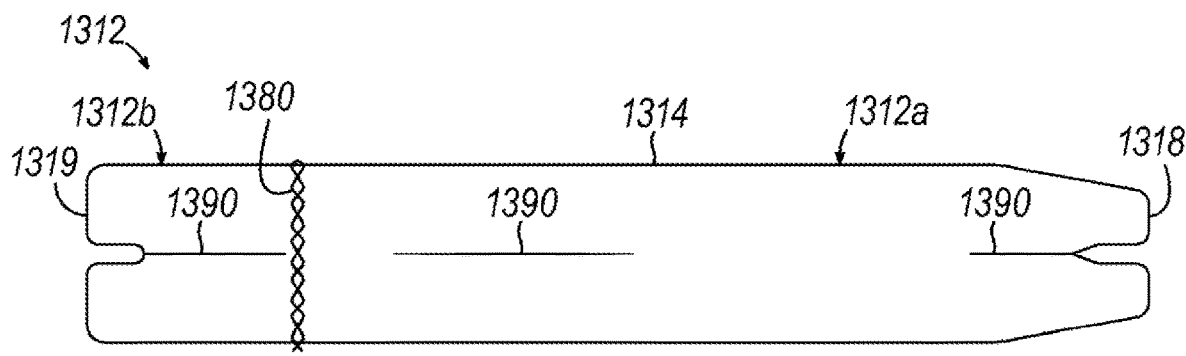
FIG. 24 depicts a top plan view of another exemplary buttress assembly having a purse string suture for facilitating adjustment of the buttress assembly to a predetermined length.

FIG. 24 shows another exemplary adjunct element in the form of a buttress assembly (1312) having separable proximal and distal portions (1312a, 1312b) configured to facilitate adjustment of the length of buttress assembly (1312). Buttress assembly (1312) is similar to buttress assemblies (110, 112) described above, except as otherwise described below. In this regard, buttress assembly (1312) of this example comprises a buttress body (1314) extending longitudinally between proximal and distal ends (1318, 1319). Buttress assembly (1312) may also comprise at least one adhesive bead or other type of adhesive layer (not shown) for adhering buttress body (1314) to underside (124) of anvil (18) or to upper deck (72) of staple cartridge (37). In some versions, buttress assembly (1312) may have an initial length of approximately 60 mm.

Buttress assembly (1312) of the present example further includes a variable length feature in the form of a purse string suture (1380) removably coupling proximal and distal portions of buttress body (1314) to each other and configured to be selectively removed from buttress assembly (1312) to thereby shorten buttress assembly (1312) from the initial length to a predetermined subsequent length. More particularly, purse string suture (1380) may be pulled from buttress assembly (1312) by the operator to detach a scrap distal portion (1312b) of buttress assembly (1312) from a desired proximal portion (1312a) of buttress assembly (1312) having the predetermined subsequent length, without requiring the use of a blade or other cutting element.

Purse string suture (1380) of the present example defines a detachment line that is generally perpendicular to the longitudinal direction and that is positioned at a predetermined distance from proximal end (1318) of buttress body (1314) corresponding to the predetermined subsequent length, such that the cutting line delineates proximal and distal portions (1312a, 1312b) of buttress assembly (1312). For example, purse string suture (1380) may be positioned approximately 45 mm from proximal end (1318) such that removal of purse string suture (1380) may shorten buttress assembly (1312) to a predetermined subsequent length of approximately 45 mm. It will be appreciated that purse string suture (1380) may be positioned at any other suitable distance from proximal end (1318) and/or may be suitably positioned relative to any other reference portion of buttress assembly (1312) for facilitating shortening of buttress assembly (1312). In some versions, the position of purse string suture (1380) may be fine-tuned to maximize a number of staples straddling purse string suture (1380) in operations where buttress assembly (1312) is used while maintaining the initial length of buttress assembly (1312). While a single purse string suture (1380) is shown for facilitating shortening of buttress assembly (1312) to a single predetermined subsequent length, multiple purse string sutures (1380) may be provided along the length of buttress body (1314) for facilitating shortening of buttress assembly (1312) to any number of predetermined subsequent lengths.

While purse string suture (1380) is shown incorporated into buttress assembly (1312) having the configuration described above, it will be appreciated that purse string suture (1380) may be readily incorporated into a buttress assembly having any other suitable configuration, such as a generally rectangular configuration similar to that shown in FIGS. 18A-18C.

Buttress assembly (1312) also comprises multiple slits (1390) that extend longitudinally along buttress body (1314) to generally divide buttress body (1314) into two equal sections. Referring to FIG. 10, when buttress assembly (1312) is used with end effector (12) in a cutting and stapling procedure, cutting edge (48) of firing beam (14) will travel longitudinally through end effector (12) to cut clamped tissue and at the same time cut buttress body (1314) of buttress assembly (1312) along slits (1390). This creates the cut and stapled site as illustrated in FIG. 10. Slits (1390) act as precuts in buttress body (1314) such that during a cutting and stapling action, buttress body (1314) offers less resistance to being cut, which promotes buttress body (1314) remaining properly placed relative to the surgically cut and stapled site, instead of buttress body (1314) being pushed longitudinally by cutting edge (48) and bunching. While the present example uses slits (1390) to precut and promote ease of cutting buttress body (1314), in view of the teachings herein, other techniques and precut geometries can be used and will be apparent to those of ordinary skill in the art.

F. Exemplary Buttress Assembly with Bridge Attachment

Figure 25:
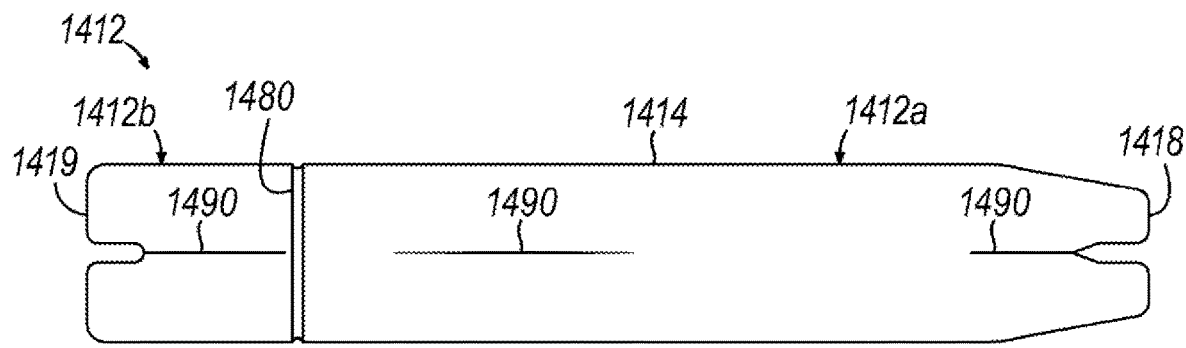
FIG. 25 depicts a top plan view of another exemplary buttress assembly having a frangible bridge for facilitating adjustment of the buttress assembly to a predetermined length.

FIG. 25 shows another exemplary adjunct element in the form of a buttress assembly (1412) having separable proximal and distal portions (1412a, 1412b) configured to facilitate adjustment of the length of buttress assembly (1412). Buttress assembly (1412) is similar to buttress assemblies (110, 112) described above, except as otherwise described below. In this regard, buttress assembly (1412) of this example comprises a buttress body (1414) extending longitudinally between proximal and distal ends (1418, 1419). Buttress assembly (1412) may also comprise at least one adhesive bead or other type of adhesive layer (not shown) for adhering buttress body (1414) to underside (124) of anvil (18) or to upper deck (72) of staple cartridge (37). In some versions, buttress assembly (1412) may have an initial length of approximately 60 mm.

Buttress assembly (1412) of the present example further includes a variable length feature in the form of a frangible bridge (1480) removably coupling proximal and distal portions of buttress body (1414) to each other and configured to be selectively removed from buttress assembly (1412) to thereby shorten buttress assembly (1412) from the initial length to a predetermined subsequent length. More particularly, frangible bridge (1480) may be torn or otherwise fractured by the operator to detach a scrap distal portion (1412*b*) of buttress assembly (1412) from a desired proximal portion (1412*a*) of buttress assembly (1412) having the predetermined subsequent length, without requiring the use of a blade or other cutting element. In this regard, frangible bridge (1480) may be defined by a structurally weakened portion of buttress body (1410). For example, the remainder of buttress body (1410) may include a mesh of polyglactin 910 material, laminated between top and bottom layers of a polymeric material, such as polydioxanone (PDO), while the structurally weakened portion of buttress body (1410) defining frangible bridge (1480) may include only the top and bottom layers of polymeric material. In other words, the mesh may not extend across frangible bridge (1480) such that frangible bridge (1480) may be structurally weak relative to the remainder of buttress body (1410).

Frangible bridge (1480) of the present example defines a detachment line that is generally perpendicular to the longitudinal direction and that is positioned at a predetermined distance from proximal end (1418) of buttress body (1414) corresponding to the predetermined subsequent length, such that the detachment line delineates proximal and distal portions (1412*a*, 1412*b*) of buttress assembly (1412). For example, frangible bridge (1480) may be positioned approximately 45 mm from proximal end (1418) such that fracturing of frangible bridge (1480) may shorten buttress assembly (1412) to a predetermined subsequent length of approximately 45 mm. It will be appreciated that frangible bridge (1480) may be positioned at any other suitable distance from proximal end (1418) and/or may be suitably positioned relative to any other reference portion of buttress assembly (1412) for facilitating shortening of buttress assembly (1412). In some versions, the position of frangible bridge (1480) may be fine-tuned to maximize a number of staples straddling frangible bridge (1480) in operations where buttress assembly (1412) is used while maintaining the initial length of buttress assembly (1412). While a single frangible bridge (1480) is shown for facilitating shortening of buttress assembly (1412) to a single predetermined subsequent length, multiple frangible bridges (1480) may be provided along the length of buttress body (1414) for facilitating shortening of buttress assembly (1412) to any number of predetermined subsequent lengths.

While frangible bridge (1480) is shown incorporated into buttress assembly (1412) having the configuration described above, it will be appreciated that frangible bridge (1480) may be readily incorporated into a buttress assembly having any other suitable configuration, such as a generally rectangular configuration similar to that shown in FIGS. 18A-18C.

Buttress assembly (1412) also comprises multiple slits (1490) that extend longitudinally along buttress body (1414) to generally divide buttress body (1414) into two equal sections. Referring to FIG. 10, when buttress assembly (1412) is used with end effector (12) in a cutting and stapling procedure, cutting edge (48) of firing beam (14) will travel longitudinally through end effector (12) to cut clamped tissue and at the same time cut buttress body (1414) of buttress assembly (1412) along slits (1490). This creates the cut and stapled site as illustrated in FIG. 10. Slits (1490) act as precuts in buttress body (1414) such that during a cutting and stapling action, buttress body (1414) offers less resistance to being cut, which promotes buttress body (1414) remaining properly placed relative to the surgically cut and stapled site, instead of buttress body (1414) being pushed longitudinally by cutting edge (48) and bunching. While the present example uses slits (1490) to precut and promote ease of cutting buttress body (1414), in view of the teachings herein, other techniques and precut geometries can be used and will be apparent to those of ordinary skill in the art.

G. Exemplary Buttress Assembly with Separation Gap

Figure 26:
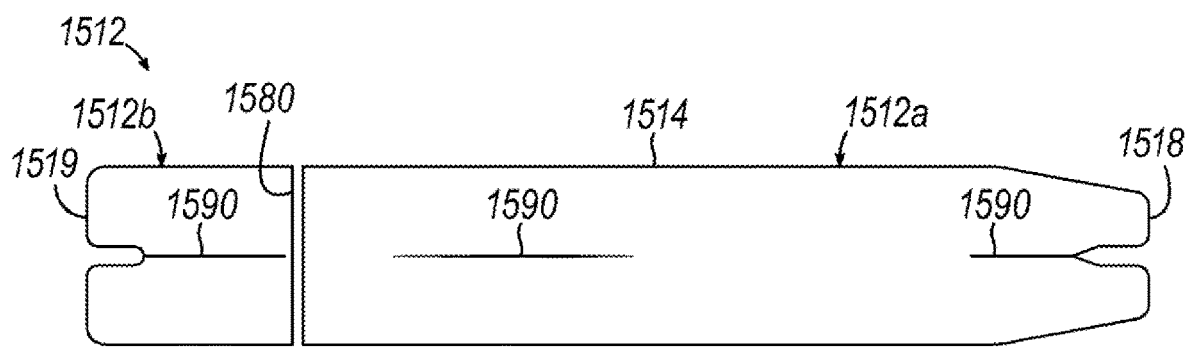
FIG. 26 depicts a top plan view of another exemplary buttress assembly having a separation gap for facilitating adjustment of the buttress assembly to a predetermined length.

FIG. 26 shows another exemplary adjunct element in the form of a buttress assembly (1512) having separable proximal and distal portions (1512*a*, 1512*b*) configured to facilitate adjustment of the length of buttress assembly (1512). Buttress assembly (1512) is similar to buttress assemblies (110, 112) described above, except as otherwise described below. In this regard, buttress assembly (1512) of this example comprises a buttress body (1514) extending longitudinally between proximal and distal ends (1518, 1519). Buttress assembly (1512) may also comprise at least one adhesive bead or other type of adhesive layer (not shown) for adhering buttress body (1514) to underside (124) of anvil (18) or to upper deck (72) of staple cartridge (37). In some versions, buttress assembly (1512) may have an initial length of approximately 60 mm.

Buttress assembly (1512) of the present example further includes a variable length feature in the form of a gap (1580) separating proximal and distal portions of buttress body (1514) from each other and configured to permit shortening of buttress assembly (1512) from the initial length to a predetermined subsequent length. More particularly, gap (1580) may permit the operator to discard scrap distal portion (1512*b*) of buttress assembly (1512) without first requiring the operator to detach scrap distal portion (1512*b*) from a desired proximal portion (1512*a*) of buttress assembly (1512) having the predetermined subsequent length, without requiring the use of a blade or other cutting element.

Gap (1580) of the present example defines a separation line that is generally perpendicular to the longitudinal direction and that is positioned at a predetermined distance from proximal end (1518) of buttress body (1514) corresponding to the predetermined subsequent length, such that the separation line delineates proximal and distal portions (1512*a*, 1512*b*) of buttress assembly (1512). For example, gap (1580) may be positioned approximately 45 mm from proximal end (1518) such that gap (1580) may permit shortening of buttress assembly (1512) to a predetermined subsequent length of approximately 45 mm. It will be appreciated that gap (1580) may be positioned at any other suitable distance from proximal end (1518) and/or may be suitably positioned relative to any other reference portion of buttress assembly (1512) for facilitating shortening of buttress assembly (1512). In some versions, the position of gap (1580) may be fine-tuned to maximize a number of staples straddling gap (1580) in operations where buttress assembly (1512) is used while maintaining the initial length of buttress assembly (1512). While a single gap (1580) is shown for facilitating shortening of buttress assembly (1512) to a single predetermined subsequent length, multiple gaps (1580) may be provided along the length of buttress body (1514) for facilitating shortening of buttress assembly (1512) to any number of predetermined subsequent lengths.

While gap (1580) is shown incorporated into buttress assembly (1512) having the configuration described above, it will be appreciated that gap (1580) may be readily incorporated into a buttress assembly having any other suitable configuration, such as a generally rectangular configuration similar to that shown in FIGS. 18A-18C.

Buttress assembly (1512) also comprises multiple slits (1590) that extend longitudinally along buttress body (1514) to generally divide buttress body (1514) into two equal sections. Referring to FIG. 10, when buttress assembly (1512) is used with end effector (12) in a cutting and stapling procedure, cutting edge (48) of firing beam (14) will travel longitudinally through end effector (12) to cut clamped tissue and at the same time cut buttress body (1514) of buttress assembly (1512) along slits (1590). This creates the cut and stapled site as illustrated in FIG. 10. Slits (1590) act as precuts in buttress body (1514) such that during a cutting and stapling action, buttress body (1514) offers less resistance to being cut, which promotes buttress body (1514) remaining properly placed relative to the surgically cut and stapled site, instead of buttress body (1514) being pushed longitudinally by cutting edge (48) and bunching. While the present example uses slits (1590) to precut and promote ease of cutting buttress body (1514), in view of the teachings herein, other techniques and precut geometries can be used and will be apparent to those of ordinary skill in the art.

H. Exemplary Buttress Assembly with Perforated Attachment

Figure 27:
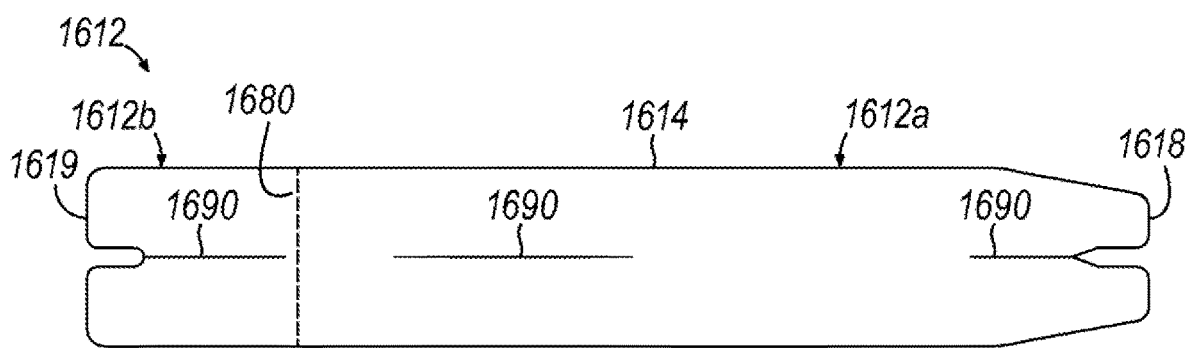
FIG. 27 depicts a top plan view of another exemplary buttress assembly having a row of perforation slits for facilitating adjustment of the buttress assembly to a predetermined length.

FIG. 27 shows another exemplary adjunct element in the form of a buttress assembly (1612) having separable proximal and distal portions (1612a, 1612b) configured to facilitate adjustment of the length of buttress assembly (1612). Buttress assembly (1612) is similar to buttress assemblies (110, 112) described above, except as otherwise described below. In this regard, buttress assembly (1612) of this example comprises a buttress body (1614) extending longitudinally between proximal and distal ends (1618, 1619). Buttress assembly (1612) may also comprise at least one adhesive bead or other type of adhesive layer (not shown) for adhering buttress body (1614) to underside (124) of anvil (18) or to upper deck (72) of staple cartridge (37). In some versions, buttress assembly (1612) may have an initial length of approximately 60 mm.

Buttress assembly (1612) of the present example further includes a variable length feature in the form of a plurality of perforation slits (1680) positioned between proximal and distal portions of buttress body (1614) and configured to enable tearing of buttress body (1614) therealong to thereby shorten buttress assembly (1612) from the initial length to a predetermined subsequent length. More particularly, buttress body (1614) may be torn or otherwise fractured by the operator along perforation slits (1680) to detach a scrap distal portion (1612b) of buttress assembly (1612) from a desired proximal portion (1612a) of buttress assembly (1612) having the predetermined subsequent length, without requiring the use of a blade or other cutting element.

Perforation slits (1680) of the present example collectively define a detachment line that is generally perpendicular to the longitudinal direction and that is positioned at a predetermined distance from proximal end (1618) of buttress body (1614) corresponding to the predetermined subsequent length, such that the detachment line delineates proximal and distal portions (1612a, 1612b) of buttress assembly (1612). For example, perforation slits (1680) may be positioned approximately 45 mm from proximal end (1618) such that tearing of buttress body (1614) therealong may shorten buttress assembly (1612) to a predetermined subsequent length of approximately 45 mm. It will be appreciated that perforation slits (1680) may be positioned at any other suitable distance from proximal end (1618) and/or may be suitably positioned relative to any other reference portion of buttress assembly (1612) for facilitating shortening of buttress assembly (1612). In some versions, the position of perforation slits (1680) may be fine-tuned to maximize a number of staples straddling perforation slits (1680) in operations where buttress assembly (1612) is used while maintaining the initial length of buttress assembly (1612). While a single row of perforation slits (1680) is shown for facilitating shortening of buttress assembly (1612) to a single predetermined subsequent length, multiple rows of perforation slits (1680) may be provided along the length of buttress body (1614) for facilitating shortening of buttress assembly (1612) to any number of predetermined subsequent lengths.

While perforation slits (1680) are shown incorporated into buttress assembly (1612) having the configuration described above, it will be appreciated that perforation slits (1680) may be readily incorporated into a buttress assembly having any other suitable configuration, such as a generally rectangular configuration similar to that shown in FIGS. 18A-18C.

Buttress assembly (1612) also comprises multiple slits (1690) that extend longitudinally along buttress body (1614) to generally divide buttress body (1614) into two equal sections. Referring to FIG. 10, when buttress assembly (1612) is used with end effector (12) in a cutting and stapling procedure, cutting edge (48) of firing beam (14) will travel longitudinally through end effector (12) to cut clamped tissue and at the same time cut buttress body (1614) of buttress assembly (1612) along slits (1690). This creates the cut and stapled site as illustrated in FIG. 10. Slits (1690) act as precuts in buttress body (1614) such that during a cutting and stapling action, buttress body (1614) offers less resistance to being cut, which promotes buttress body (1614) remaining properly placed relative to the surgically cut and stapled site, instead of buttress body (1614) being pushed longitudinally by cutting edge (48) and bunching. While the present example uses slits (1690) to precut and promote ease of cutting buttress body (1614), in view of the teachings herein, other techniques and precut geometries can be used and will be apparent to those of ordinary skill in the art.

Exemplary Alternative Buttress Assembly with Notches

Figure 28:
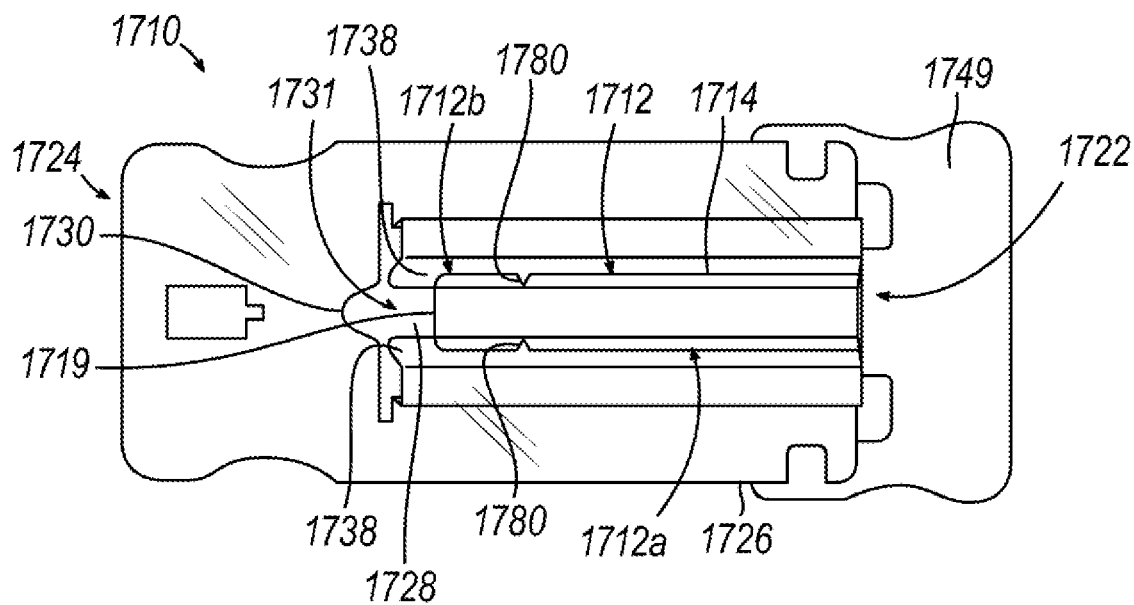
FIG. 28 depicts a top plan view of another buttress applicator carrying another exemplary buttress assembly having a laterally-opposed pair of notches for facilitating adjustment of the buttress assembly to a predetermined length.
Figure 29:
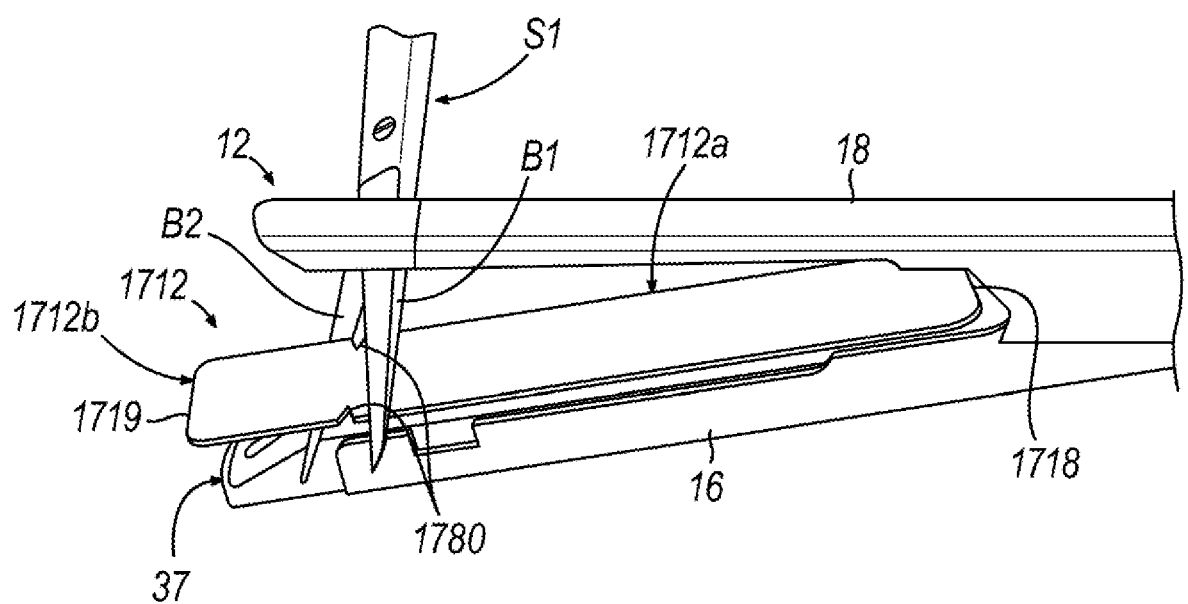
FIG. 29 depicts a perspective view of the buttress assembly of FIG. 28, showing the buttress assembly applied to an end effector jaw, and further showing scissors trimming the buttress assembly.

FIGS. 28-29 show another buttress applicator (1710) for applying another exemplary buttress assembly (1712) to at least one jaw of an end effector, such as at least one jaw (16, 18) of end effector (12). Buttress assembly (1712) has separable proximal and distal portions (1712a, 1712b) configured to facilitate adjustment of the length of buttress assembly (1712). Buttress applicator (1710) and buttress assembly (1712) are similar to buttress applicator (210) and buttress assemblies (110, 112) described above, respectively, except as otherwise described below. In this regard, buttress assembly (1712) of this example comprises a buttress body (1714), which may be substantially transparent and/or translucent, extending longitudinally between proximal and distal ends (1718, 1719). Buttress assembly (1712) may also comprise at least one adhesive bead or other type of adhesive layer (not shown) for adhering buttress body (1714) to underside (124) of anvil (18) or to upper deck (72) of staple cartridge (37). Buttress body (1714) may comprise PERI-STRIPS DRY with VERITAS Collagen Matrix (PSDV) reinforcement material, by Baxter Healthcare Corporation of Deerfield, Ill., for example. In some versions, buttress assembly (1712) may have an initial length of approximately 60 mm.

Buttress applicator (1710) of this example comprises an open end (1722) and a closed end (1724). Open end (1722)

is configured to receive end effector (12) in a manner similar to that described above in connection with FIGS. 13A-13B. Buttress applicator (1710) further includes at least one housing (1726) which generally defines a "U" shape to present open end (1722). A platform (1728) extends longitudinally between a proximal end (not shown) and a distal end (1730) and is exposed in one or more recesses (1731) that are formed between the prongs of the "U" configuration of housing (1726) and is configured to support buttress assembly (1712) on an upper side of platform (1728), though platform (1728) may just as easily support another buttress assembly (1712) on a lower side of platform (1728). While buttress assembly (1712) is illustrated as a relatively wide version that may unitarily span across slot (42) of anvil (18) or slot (49) of staple cartridge (37), buttress assembly (1712) may be provided in a pair of portions that are separated to avoid spanning across either slot (42, 49). In any event, a plurality of flanges (1738) are configured to resiliently bear against buttress assembly (1712), thereby pinching buttress assembly (1712) against platform (1728) to selectively secure buttress assembly (1712) to platform (1728). A buttress retainer (1749) is removably coupled to open end (1722).

Buttress assembly (1712) of the present example further includes a variable length feature in the form of a laterally-opposed pair of notches (1780) similar to notches (980) described above in connection with FIG. 20. As shown, notches (1780) extend partially through buttress body (1714) and identify a visible path for guiding one or more blades (B1, B2) of scissors (S1) across buttress assembly (1712) to thereby shorten buttress assembly (1712) from the initial length to a predetermined subsequent length. More particularly, notches (1780) may identify the path for guiding blade(s) (B1, B2) to sever a scrap distal portion (1712b) of buttress assembly (1712) from a desired proximal portion (1712a) of buttress assembly (1712) having the predetermined subsequent length, as shown in FIG. 29. In the version shown, scrap distal portion (1712b) is severed from desired proximal portion (1712a) after desired proximal portion (1712a) of buttress assembly (1712) has been adhesively attached to staple cartridge (37) (or anvil (18)). In other versions, scrap distal portion (1712b) may be severed from desired proximal portion (1712a) while still positioned on the upper side of platform (1728). In such cases, flanges (1738) may continue to secure scrap distal portion (1712b) of buttress assembly (1712) to platform (1728) after desired proximal portion (1712a) of buttress assembly (1712) has been severed and applied to staple cartridge (37) (or anvil (18)).

While buttress assembly (1712) is shown having a variable length feature in the form of notches (1780), buttress assembly (1712) may additionally or alternatively have any one or more of the other variable length features described above in connection with FIGS. 21-27. For example, buttress assembly (1712) may include indicia similar to any one or more of indicia (1080, 1180, 1280), a purse string suture similar to purse string suture (1380), a frangible bridge similar to frangible bridge (1480), a gap similar to gap (1580), and/or perforation slits similar to perforation slits (1680).

J. Exemplary Buttress Tube with Visual Cutting Indicia

Figure 30A:
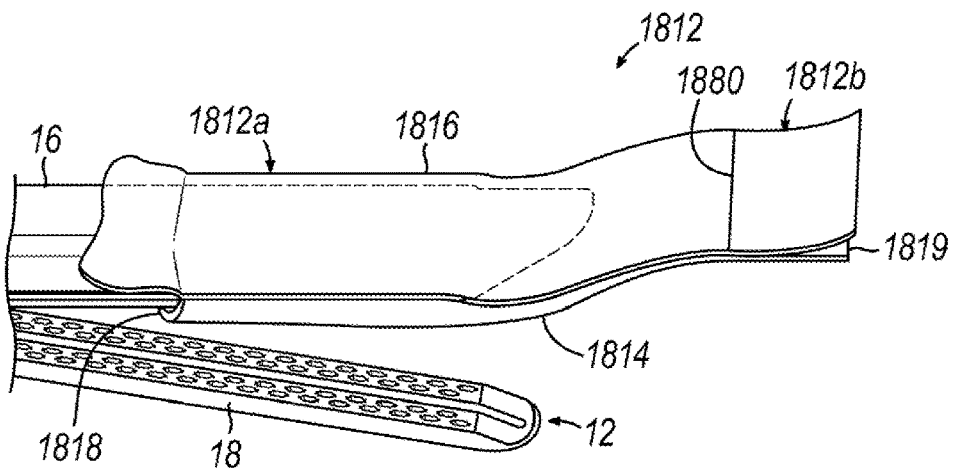
FIG. 30A depicts a perspective view of another exemplary buttress assembly having visual indicia for facilitating adjustment of the buttress assembly to a predetermined length, showing the buttress assembly applied to an end effector jaw.
Figure 30B:
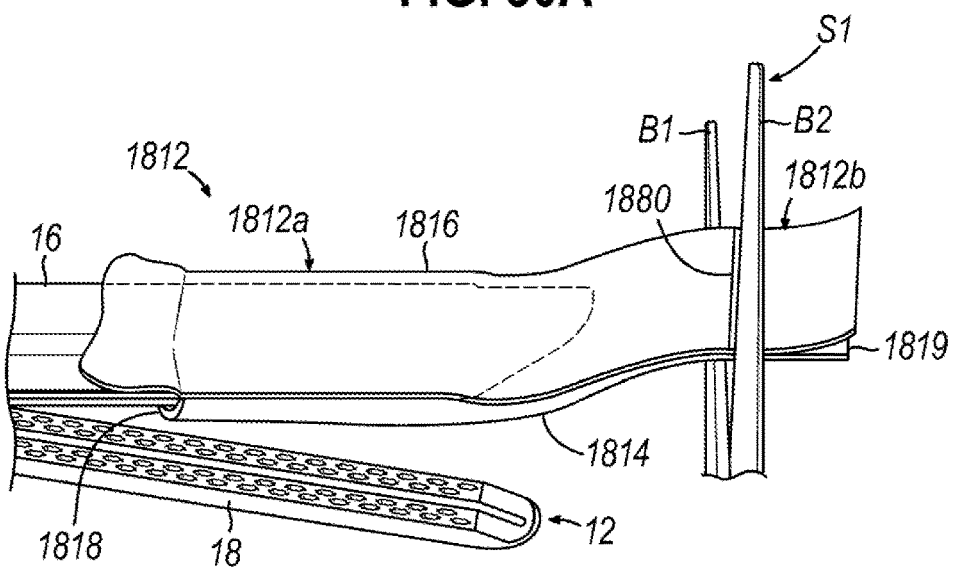
FIG. 30B depicts a perspective view of the buttress assembly of FIG. 30A, showing scissors trimming the buttress assembly.
Figure 30C:
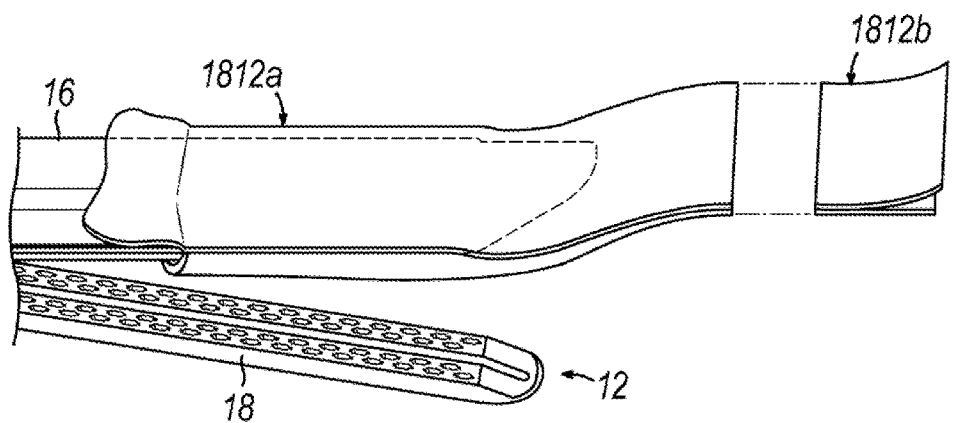
FIG. 30C depicts a perspective view of the buttress assembly of FIG. 30A, showing a distal portion of the buttress assembly discarded from a proximal portion of the buttress assembly.

FIGS. 30A-30C show another exemplary buttress assembly (1812) having separable proximal and distal portions (1812a, 1812b) configured to facilitate adjustment of the length of buttress assembly (1812), and configured for application to at least one jaw of an end effector, such as at least one jaw (16, 18) of end effector (12). Buttress assembly (1812) is similar to buttress assemblies (110, 112) described above, except as otherwise described below. In this regard, buttress assembly (1812) of this example comprises a buttress body (1814) extending longitudinally between proximal and distal ends (1818, 1819), and further includes an application backing (1816) removably coupled to buttress body (1814) along lateral sides thereof via one or more sutures (not shown) such that buttress assembly (1812) has a generally tubular shape. Backing (1816) may assist with securing buttress body (1814) to upper deck (72) of staple cartridge (37) (or to underside (124) of anvil (18)), such as by capturing upper deck (72) of staple cartridge (37) (or underside (124) of anvil (18)) between buttress body (1814) and backing (1816), as shown in FIG. 30A. Buttress body (1814) may comprise NEOVEIL absorbable PGA felt by Gunze Limited, of Kyoto, Japan, for example. In some versions, buttress assembly (1812) may have an initial length of approximately 60 mm.

Buttress assembly (1812) of the present example further includes a variable length feature in the form of a cutting indicia (1880) similar to indicia (1080) described above in connection with FIG. 21. As shown, indicia (1880) is provided on buttress body (1814) and identifies a visible path (e.g., by including a visually discernible line) for guiding one or more blades (B1, B2) of scissors (S1) across buttress assembly (1812) to thereby shorten buttress assembly (1812) from the initial length to a predetermined subsequent length. More particularly, indicia (1880) may identify the path for guiding blade(s) (B1, B2) to sever a scrap distal portion (1812b) of buttress assembly (1812) from a desired proximal portion (1812a) of buttress assembly (1812) having the predetermined subsequent length, as shown in FIG. 30B. In the version shown, scrap distal portion (1812b) is severed from desired proximal portion (1812a) after desired proximal portion (1812a) of buttress assembly (1812) has been secured to staple cartridge (37) (or anvil (18)), as shown in FIG. 30C. In other versions, scrap distal portion (1812b) may be severed from desired proximal portion (1812a) prior to securing desired proximal portion (1812a) of buttress assembly (1812) to staple cartridge (37) (or anvil (18)). In any event, the sutures of buttress assembly (1812) may be pulled by the operator after jaws (16, 18) have been closed to clamp tissue therebetween, thereby detaching backing (1816) from proximal portion (1812a) of buttress assembly (1812).

While buttress assembly (1812) is shown having a variable length feature in the form of indicia (1880), buttress assembly (1812) may additionally or alternatively have any one or more of the other variable length features described above in connection with FIGS. 20 and 22-27. For example, buttress assembly (1812) may include notches similar to notches (980), indicia similar to any one or more of indicia (1180, 1280), a purse string suture similar to purse string suture (1380), a frangible bridge similar to frangible bridge (1480), a gap similar to gap (1580), and/or perforation slits similar to perforation slits (1680).

Figure 31:
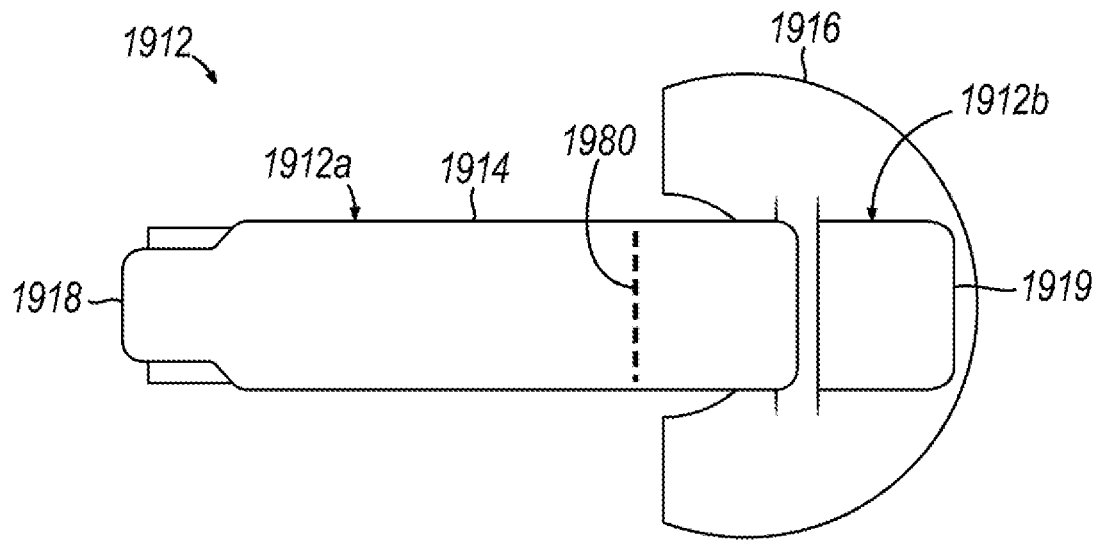
FIG. 31 depicts a top plan view of another exemplary buttress assembly having visual indicia for facilitating adjustment of the buttress assembly to a predetermined length.

K. Exemplary Alternative Cartridge Buttress Assembly with Visual Cutting Indicia FIG. 31 shows another exemplary buttress assembly (1912) having separable proximal and distal portions (1912a, 1912b) configured to facilitate adjustment of the length of buttress assembly (1912), and configured for application to at least one jaw of an end effector, such as lower jaw (16) of end effector (12). Buttress assembly (1912) is similar to buttress assemblies (110, 112) described above, except as otherwise described below. In this regard, buttress assembly (1912) of this example comprises a buttress body (1914) extending longitudinally between proximal and distal ends (1918, 1919). An application insert (1916) is removably coupled to buttress body (1914) at or near proximal and distal ends (1918, 1919). Insert (1916) may assist with application of buttress body (1914) to upper deck (72) of staple cartridge (37). In some versions, buttress assembly (1912) may further include sutures (not shown) configured to secure buttress body (1914) to upper deck (72) of staple cartridge (37). Buttress body (1914) may comprise SEAMGUARD polyglycolic acid:trimethylene carbonate (PGA:TMC) reinforcement material by W.L. Gore & Associates, Inc., of Flagstaff, Ariz., for example. In some versions, buttress assembly (1912) may have an initial length of approximately 60 mm.

Buttress assembly (1912) of the present example further includes a variable length feature in the form of a cutting indicia (1980) similar to indicia (1080) described above in connection with FIG. 21. As shown, indicia (1980) is provided on buttress body (1914) and identifies a visible path (e.g., by including a visually discernible broken line) for guiding one or more blades (not shown) across buttress assembly (1912) to thereby shorten buttress assembly (1912) from the initial length to a predetermined subsequent length. More particularly, indicia (1980) may identify the path for guiding such a blade to sever a scrap distal portion (1912b) of buttress assembly (1912) from a desired proximal portion (1912a) of buttress assembly (1912) having the predetermined subsequent length. In some versions, scrap distal portion (1912b) is severed from desired proximal portion (1912a) after desired proximal portion (1912a) of buttress assembly (1912) has been secured to staple cartridge (37). In other versions, scrap distal portion (1912b) may be severed from desired proximal portion (1912a) prior to securing desired proximal portion (1912a) of buttress assembly (1912) to staple cartridge (37). In any event, insert (1916) may be detached from proximal portion (1912a) of buttress assembly (1912) by the operator after scrap distal portion (1912b) has been severed from desired proximal portion (1912a).

Figure 32:
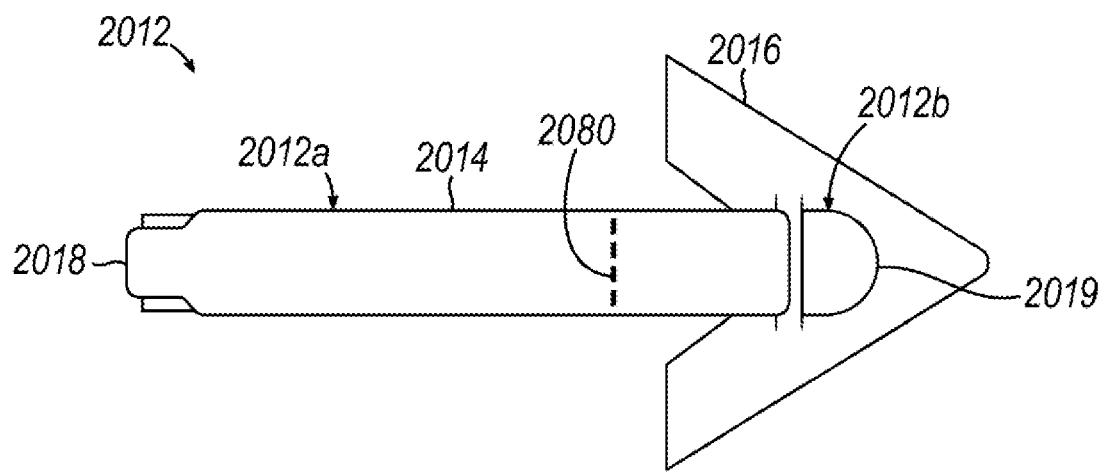
FIG. 32 depicts a top plan view of another exemplary buttress assembly having visual indicia for facilitating adjustment of the buttress assembly to a predetermined length.
Figure 33A:
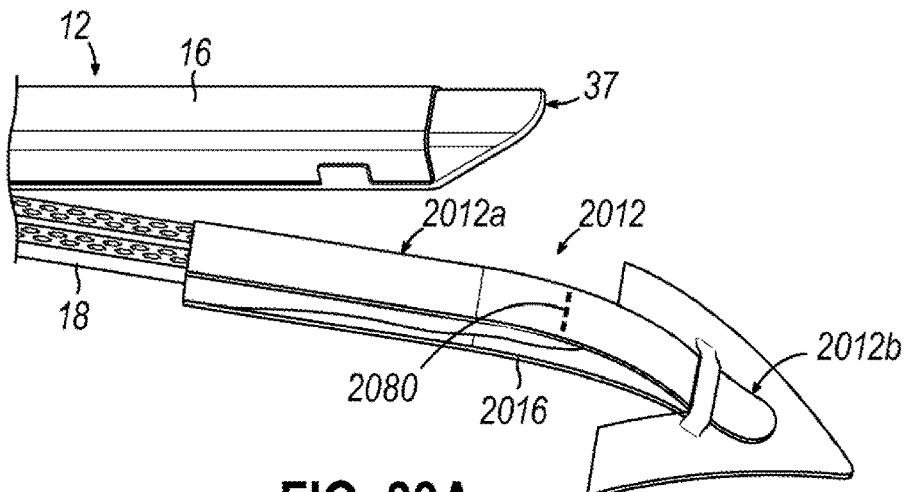
FIG. 33A depicts a perspective view of the buttress assembly of FIG. 32, showing the buttress assembly applied to an end effector jaw.
Figure 33B:
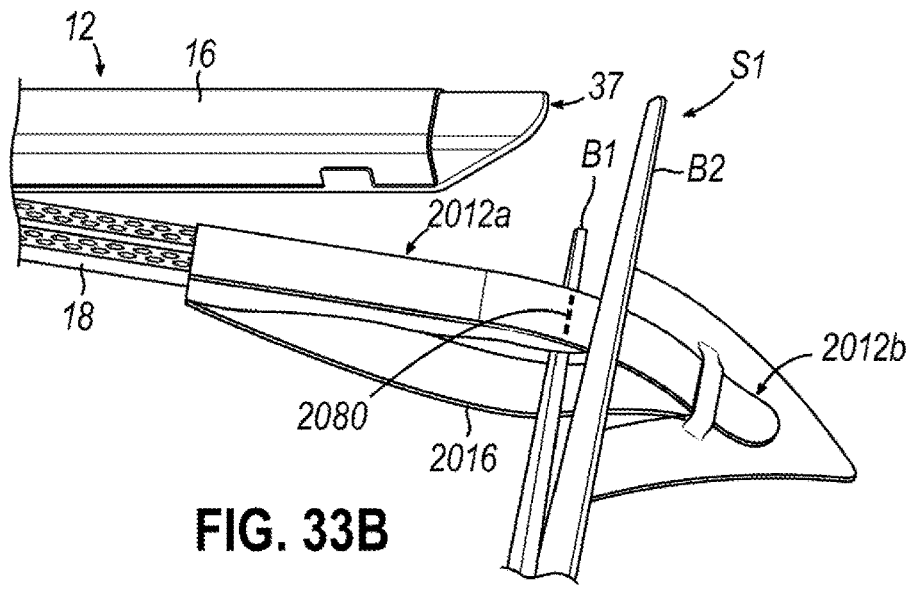
FIG. 33B depicts a perspective view of the buttress assembly of FIG. 32, showing scissors trimming the buttress assembly.
Figure 33C:
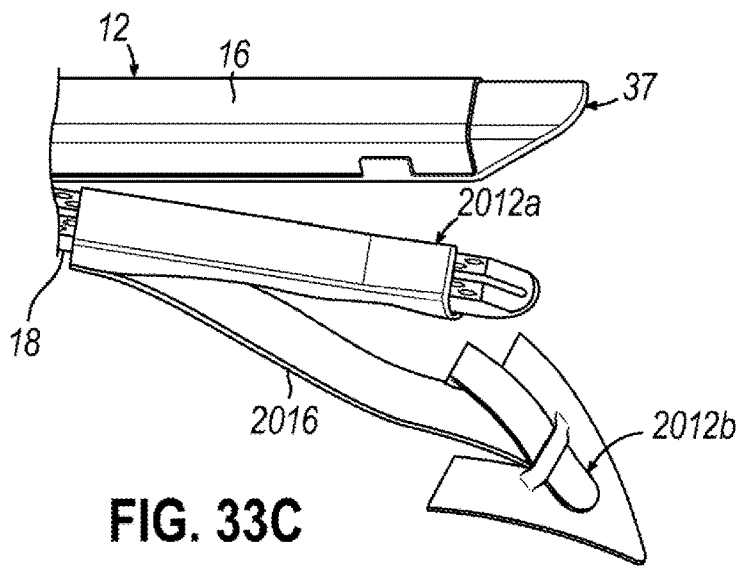
FIG. 33C depicts a perspective view of the buttress assembly of FIG. 32, showing a distal portion of the buttress assembly discarded from a proximal portion of the buttress assembly.

While buttress assembly (1912) is shown having a variable length feature in the form of indicia (1980), buttress assembly (1912) may additionally or alternatively have any one or more of the other variable length features described above in connection with FIGS. 20 and 22-27. For example, buttress assembly (1912) may include notches similar to notches (980), indicia similar to any one or more of indicia (1180, 1280), a purse string suture similar to purse string suture (1380), a frangible bridge similar to frangible bridge (1480), a gap similar to gap (1580), and/or perforation slits similar to perforation slits L. Exemplary Alternative Anvil Buttress Assembly with Visual Cutting Indicia FIGS. 32-33C show another exemplary buttress assembly (2012) having separable proximal and distal portions (2012a, 2012b) configured to facilitate adjustment of the length of buttress assembly (2012), and configured for application to at least one jaw of an end effector, such as anvil (18) of end effector (12). Buttress assembly (2012) is similar to buttress assemblies (110, 112) described above, except as otherwise described below. In this regard, buttress assembly (2012) of this example comprises a buttress body (2014) extending longitudinally between proximal and distal ends (2018, 2019). An application insert (2016) is removably coupled to buttress body (2014) at or near proximal and distal ends (2018, 2019). Insert (2016) may assist with application of buttress body (2014) to underside (124) of anvil (18). In some versions, buttress assembly (2012) may further include sutures (not shown) configured to secure buttress body (2014) to underside (124) of anvil (18), as shown in FIG. 33A. Buttress body (2014) may comprise SEAMGUARD polyglycolic acid:trimethylene carbonate (PGA:TMC) reinforcement material by W.L. Gore & Associates, Inc., of Flagstaff, Ariz., for example. In some versions, buttress assembly (2012) may have an initial length of approximately 60 mm.

Buttress assembly (2012) of the present example further includes a variable length feature in the form of a cutting indicia (2080) similar to indicia (1080) described above in connection with FIG. 21. As shown, indicia (2080) is provided on buttress body (2014) and identifies a visible path (e.g., by including a visually discernible broken line) for guiding one or more blades (B1, B2) of scissors (S1) across buttress assembly (2012) to thereby shorten buttress assembly (2012) from the initial length to a predetermined subsequent length. More particularly, indicia (2080) may identify the path for guiding blade(s) (B1, B2) to sever a scrap distal portion (2012b) of buttress assembly (2012) from a desired proximal portion (2012a) of buttress assembly (2012) having the predetermined subsequent length, as shown in FIG. 33B. In the version shown, scrap distal portion (2012b) is severed from desired proximal portion (2012a) and desired proximal portion (2012a) is slid proximally along underside (124) of anvil (18) after desired proximal portion (2012a) of buttress assembly (2012) has been positioned over underside (124) of anvil (18), as shown in FIG. 33C. In other versions, scrap distal portion (2012b) may be severed from desired proximal portion (2012a) prior to positioning desired proximal portion (2012a) of buttress assembly (2012) over underside (124) of anvil (18). In any event, insert (2016) may be detached from proximal portion (2012a) of buttress assembly (2012) by the operator after scrap distal portion (2012b) has been severed from desired proximal portion (2012a).

While buttress assembly (2012) is shown having a variable length feature in the form of indicia (2080), buttress assembly (2012) may additionally or alternatively have any one or more of the other variable length features described above in connection with FIGS. 20 and 22-27. For example, buttress assembly (2012) may include notches similar to notches (980), indicia similar to any one or more of indicia (1180, 1280), a purse string suture similar to purse string suture (1380), a frangible bridge similar to frangible bridge (1480), a gap similar to gap (1580), and/or perforation slits similar to perforation slits (1680).

V. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An assembly comprising: (a) an applicator, wherein the applicator includes: (i) a housing defining a gap, wherein the gap is configured to receive an end effector jaw of a surgical stapler, and (ii) a platform positioned within the gap, wherein the platform extends longitudinally between a proximal end and a distal end; (b) a first buttress assembly having a first length, wherein the first buttress assembly is positioned on at least a portion of the platform; and (c) at least one trimming feature presented by at least one of the applicator or the first buttress assembly, wherein the at least one trimming feature is configured to facilitate trimming of the first buttress assembly from the first length to a predetermined second length.

Example 2

The assembly of Example 1, wherein the at least one trimming feature defines a cutting line, wherein the at least one trimming feature is configured to facilitate trimming of the first buttress assembly from the first length to the predetermined second length along the cutting line.

Example 3

The assembly of Example 2, wherein the cutting line is positioned at a predetermined distance from the proximal end.

Example 4

The assembly of Example 3, wherein the predetermined distance is approximately 45 mm.

Example 5

The assembly of any one or more of Examples 1 through 4, wherein the at least one trimming feature includes at least one groove extending partially through the housing, wherein the at least one groove is configured to guide a blade to facilitate trimming of the first buttress assembly from the first length to the predetermined second length.

Example 6

The assembly of Example 5, wherein the at least one groove includes at least one base surface, wherein the at least one base surface is substantially flush with a surface of the platform.

Example 7

The assembly of any one or more of Examples 1 through 4, wherein the at least one trimming feature includes at least one slot extending through the housing, wherein the at least one slot is configured to guide at least one blade to facilitate trimming of the first buttress assembly from the first length to the predetermined second length.

Example 8

The assembly of Example 7, wherein the at least one slot extends through the platform.

Example 9

The assembly of any one or more of Examples 1 through 4, wherein the at least one trimming feature includes at least one visual indicium positioned on the housing, wherein the at least one visual indicia is configured to identify a visible path for a blade to facilitate trimming of the first buttress assembly from the first length to the predetermined second length.

Example 10

The assembly of Example 9, wherein the at least one visual indicium includes at least one visually discernible arrow.

Example 11

The assembly of any one or more of Examples 1 through 4, wherein the at least one trimming feature includes at least one cutting element movably coupled to the housing to facilitate trimming of the first buttress assembly from the first length to the predetermined second length.

Example 12

The assembly of Example 11, further comprising at least one groove extending partially through the housing, wherein the at least one cutting element is slidably disposed within the at least one groove.

Example 13

The assembly of any one or more of Examples 1 through 12, wherein the housing defines a U shape.

Example 14

The assembly of any one or more of Examples 1 through 13, wherein the first buttress assembly comprises: (i) a body, and (ii) an adhesive, wherein the adhesive is exposed in the gap defined by the housing.

Example 15

The assembly of any one or more of Examples 1 through 14, further comprising a second buttress assembly, wherein the first buttress assembly is positioned on a first side of the platform and the second buttress assembly is positioned on a second side of the platform disposed opposite the first side.

Example 16

An assembly comprising: (a) a tray, comprising: (i) a base, and (ii) a trimming feature movably coupled to the base; (b) an applicator positioned within the base, the applicator comprising: (i) a housing defining a gap, wherein the gap is configured to receive an end effector jaw of a surgical stapler, and (ii) a platform positioned within the gap; and (c) a first buttress assembly having a first length, wherein the first buttress assembly is positioned on at least a portion of the platform, wherein the trimming feature is operable to trim the first buttress assembly from the first length to a predetermined second length.

Example 17

A buttress assembly configured for use with an end effector of a surgical stapler, comprising: (a) a buttress body having a first length, wherein the buttress body is configured to be removably secured to a jaw of the end effector; and (b) at least one variable length feature presented by the buttress body, wherein the at least one variable length feature is configured to facilitate trimming of the buttress body from the first length to a predetermined second length, wherein the buttress body is configured to contact tissue clamped by the end effector during closure thereof, wherein the buttress body is further configured to be pierced and captured by staples ejected from the staple cartridge into the clamped tissue and thereby reinforce the engagement between the ejected staples with the clamped tissue.

Example 18

The buttress assembly of Example 17, wherein the buttress body includes a proximal portion and a distal portion, wherein the at least one variable length feature removably couples the proximal and distal portions to each other to facilitate trimming of the buttress body from the first length to the predetermined second length.

Example 19

The buttress assembly of Example 17, wherein the at least one variable length feature is configured to identify a visible path for a blade to facilitate trimming of the buttress body from the first length to the predetermined second length.

Example 20

A surgical stapler, comprising: (a) a shaft assembly having a distal end; (b) an end effector at the distal end of the shaft assembly, wherein the end effector includes: (i) a first jaw, and (ii) a second jaw, wherein the first and second jaws are operable to clamp tissue therebetween; and (c) the buttress assembly of any one or more of Examples 17 through 19, wherein the buttress body is removably secured to one of the first or second jaws.

VI. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An assembly comprising:
    (a) an applicator, wherein the applicator includes:
        (i) a housing defining a gap, wherein the gap is configured to receive an end effector jaw of a surgical stapler, and
        (ii) a platform positioned within the gap, wherein the platform extends longitudinally between a proximal end and a distal end;
    (b) a first buttress assembly having a first length, wherein the first buttress assembly is positioned on at least a portion of the platform; and
    (c) at least one trimming feature presented by at least one of the applicator or the first buttress assembly, wherein the at least one trimming feature is configured to facilitate trimming of the first buttress assembly from the first length to a predetermined second length,
    wherein the first buttress assembly comprises:
        (i) a body, and
        (ii) an adhesive, wherein the adhesive is exposed in the gap defined by the housing,
    wherein the body includes a proximal portion and a distal portion, wherein the proximal portion and the distal portion collectively define the first length, wherein the proximal portion defines the predetermined second length, wherein the adhesive is disposed on both the proximal and distal portions.

2. The assembly of claim 1, wherein the at least one trimming feature defines a cutting line, wherein the at least one trimming feature is configured to facilitate trimming of the first buttress assembly from the first length to the predetermined second length along the cutting line.

3. The assembly of claim 2, wherein the cutting line is positioned at a predetermined distance from the proximal end.

4. The assembly of claim 3, wherein the predetermined distance is 45 mm.

5. The assembly of claim 1, wherein the at least one trimming feature includes at least one groove extending partially through the housing, wherein the at least one groove is configured to guide a blade to facilitate trimming of the first buttress assembly from the first length to the predetermined second length.

6. The assembly of claim 5, wherein the at least one groove includes at least one base surface, wherein the at least one base surface is substantially flush with a surface of the platform.

7. The assembly of claim 1, wherein the at least one trimming feature includes at least one slot extending through the housing, wherein the at least one slot is configured to guide at least one blade to facilitate trimming of the first buttress assembly from the first length to the predetermined second length.

8. The assembly of claim 7, wherein the at least one slot extends through the platform.

9. The assembly of claim 1, wherein the at least one trimming feature includes at least one visual indicium positioned on the housing, wherein the at least one visual indicia is configured to identify a visible path for a blade to facilitate trimming of the first buttress assembly from the first length to the predetermined second length.

10. The assembly of claim 9, wherein the at least one visual indicium includes at least one visually discernible arrow.

11. The assembly of claim 1, wherein the at least one trimming feature includes at least one cutting element movably coupled to the housing to facilitate trimming of the first buttress assembly from the first length to the predetermined second length.

12. The assembly of claim 11, further comprising at least one groove extending partially through the housing, wherein the at least one cutting element is slidably disposed within the at least one groove.

13. The assembly of claim 1, wherein the housing defines a U shape.

14. The assembly of claim 1, further comprising a second buttress assembly, wherein the first buttress assembly is positioned on a first side of the platform and the second buttress assembly is positioned on a second side of the platform disposed opposite the first side.

15. An assembly comprising:
    (a) a tray, comprising:
        (i) a base, and
        (ii) a trimming feature pivotably coupled to the base;
    (b) an applicator positioned within the base, the applicator comprising:
        (i) a housing defining a gap, wherein the gap is configured to receive an end effector jaw of a surgical stapler, and
        (ii) a platform positioned within the gap; and
    (c) a first buttress assembly having a first length, wherein the first buttress assembly is positioned on at least a portion of the platform,
    wherein the trimming feature is operable to trim the first buttress assembly from the first length to a predetermined second length.

16. A buttress assembly configured for use with an end effector of a surgical stapler, comprising:
    (a) a buttress body having a first length, wherein the buttress body is configured to be removably secured to a jaw of the end effector;
    (b) at least one variable length feature presented by the buttress body, wherein the at least one variable length feature is configured to facilitate trimming of the buttress body from the first length to a predetermined second length and
    (c) an adhesive,
    wherein the buttress body includes a proximal portion and a distal portion, wherein the proximal portion and the distal portion collectively define the first length, wherein the proximal portion defines the predetermined second length,
    wherein the adhesive is disposed on both the proximal and distal portions,
    wherein the buttress body is configured to contact tissue clamped by the first or second end effector during closure thereof,
    wherein the buttress body is further configured to be pierced and captured by staples ejected from the staple cartridge into the clamped tissue and thereby reinforce the engagement between the ejected staples with the clamped tissue.

17. The buttress assembly of claim 16, wherein the buttress body includes a proximal portion and a distal portion, wherein the at least one variable length feature removably couples the proximal and distal portions to each other to facilitate trimming of the buttress body from the first length to the predetermined second length.

18. The buttress assembly of claim 16, wherein the at least one variable length feature is configured to identify a visible path for a blade to facilitate trimming of the buttress body from the first length to the predetermined second length.

19. The buttress assembly of claim 16, further comprising a backing removably coupled to the buttress body along lateral sides of the buttress body, wherein the buttress body and the backing collectively define a generally tubular shape.

20. An assembly comprising:
(a) an applicator, wherein the applicator includes:
   (i) a housing defining a gap, wherein the gap is configured to receive an end effector jaw of a surgical stapler, and
   (ii) a platform positioned within the gap, wherein the platform extends longitudinally between a proximal end and a distal end;
(b) a buttress assembly having a first length, wherein the buttress assembly is positioned on at least a portion of the platform; and
(c) at least one guide presented by at least one of the applicator or the buttress assembly, wherein the at least one guide is configured to facilitate trimming of the buttress assembly from the first length to a predetermined second length,
wherein the buttress assembly comprises:
   (i) a body, and
   (ii) an adhesive, wherein the adhesive is exposed in the gap defined by the housing,
wherein the body includes a proximal portion and a distal portion, wherein the proximal portion and the distal portion collectively define the first length, wherein the proximal portion defines the predetermined second length, wherein the adhesive is disposed on both the proximal and distal portions.

* * * * *